US008388547B2

(12) United States Patent
Revishvili et al.

(10) Patent No.: US 8,388,547 B2
(45) Date of Patent: Mar. 5, 2013

(54) METHOD OF NONINVASIVE ELECTROPHYSIOLOGICAL STUDY OF THE HEART

(75) Inventors: Amiran Shotaevich Revishvili, Moscow (RU); Vitaliy Viktorovich Kalinin, Voronezh (RU); Alexander Viktorovich Kalinin, Voronezh (RU)

(73) Assignee: "Amycard" LLC, Moscow (RU)

( * ) Notice: Subject to any disclaimer, the term of this patent is extended or adjusted under 35 U.S.C. 154(b) by 417 days.

(21) Appl. No.: 12/623,818

(22) Filed: Nov. 23, 2009

(65) Prior Publication Data

US 2010/0191131 A1 Jul. 29, 2010

(30) Foreign Application Priority Data

Nov. 27, 2008 (RU) ............................... 2008146994

(51) Int. Cl.
*A61B 5/0402* (2006.01)
(52) U.S. Cl. ....................................... 600/508; 600/513
(58) Field of Classification Search .................. 600/508, 600/509, 512, 513
See application file for complete search history.

(56) References Cited

U.S. PATENT DOCUMENTS 7,016,719 B2 3/2006 Rudy et al.

OTHER PUBLICATIONS

Sulimov, V. A., et al., "Transesophaegeal Cardiac Electrostimulation", Moscow, Meditsina, 2001.
Pokushalov, E. A., et al., "Radio-Frequency Transpericardial Catheter Ablation of Ventricular Tachycardia", Vestnik arimologii, 2006, No. 44.
Nelson, C. V., et al., "The Theoretical Basis of Electrocardiology", Moscow, Meditsina, 1979.
Kalinin, V. V., "Use of ECG Recorded through a Subclavian Catheter for Differential Diagnosing Tachyarrhythmias", Proceedings of the $4^{th}$ Session of MSAR, Mar. 26, 2004.
Denisov, A. M., Introduction to Theory of Inverse Problems, Moscow University Publishing House, 1994.
Tikhonov, A.N., "Methods of Solution of Incorrect Problems", Nauka, 1979.
Titomir, et al., "Mathematical Modeling of the Cardiac Bioelectric Generator", Nauka, 1999.
Lacroute, P., "Fast Volume Rendering Using a Shear-Warp Factorization of the Viewing Transformation", Technical Report: CSL-TR-95-678, Sep. 1995.
Lorensen, W., et al., "Marching Cubes: A High Resolution 3D Surface Construction Algorithm", Computer Graphics, vol. 21, No. 4, Jul. 1987.
Saad, Yousef, "Iterative Methods for Sparse Linear Systems", 2000.
Rudy, Y., et al., "The Inverse Problem in Electrocardiography: Solutions in Terms of Epicardial Potentials", Crit Rev Biomed Eng., 1988: 16(3), Abstract.
Berger, T., et al., "Single-Beat Noninvasive Imaging of Cardiac Electrophysiology of Ventricular Pre-Excitation", J. Am. Coll. Cardiol., 2006.
Lo, S. H., "Volume Discretization into Tetrahedra-II. 3D Triangulation by Advancing Front Approach", Computers & Structures, vol. 39, Issue 5, 1991, Abstract.

(Continued)

*Primary Examiner* — George Evanisko
(74) *Attorney, Agent, or Firm* — Ladas & Parry LLP

(57) ABSTRACT

The invention relates to medicine, namely to cardiology, cardiovascular surgery, functional diagnosis and clinical electrophysiology of the heart. The invention consists in reconstructing electrograms, whose experimental registration requires an invasive access, by computational way on unipolar ECGs recorded at 80 and more points of the chest surface. Based on reconstructed electrograms, isopotential, isochronous maps on realistic models of the heart are constructed, the dynamics of the myocardium excitation is reconstructed and electrophysiological processes in the cardiac muscle are diagnosed. Application of the method allows one to improve the accuracy of non-invasive diagnosis of cardiac rhythm disturbances and other cardio-vascular diseases.

15 Claims, 23 Drawing Sheets

OTHER PUBLICATIONS

Rassineaux, A., "3D Mesh Adaption, Optimization of Tetrahedral Meshes by Advancing Front Technique", Comput. Methods appl. Mech. Engrg. 141, 1997.
Yoshida, Ken-ichi, "Applications of fast Multipole Method to Boundary Integral Equation Method", Dept. of Global Environment Eng., Kyoto Univ., Japan, Mar. 2001.
Kazhdan, M., et al.,"Poisson Surface Reconstruction", Eurographics Symposium on Geometry Processing, 2006.
Schilling, R.J., "Endocardial Mapping of Atrial Fibrillation in the Human Right Atrium Using a Non-contact Catheter", European Heart Journal, (2000) 21.
Ramanathan, C., "Noninvasive Electrocardiographic Imaging for Cardiac Electrophysiology and Arrhythmia", Nature Medicine, 2004.
Brebbia, C.A., et al., "Boundary and Element Techniques: Theory and Applications in Engineering," Chapter 2, Springer-Verlag, p. 54-122, 1984, with English translation.
Revishvili, A. Sh., "Electrophysiological Diagnostics and Interventional Treatment of Complex Cardiac Arrhythmias With Use of the System of Three-Dimensional Electro-Anatomical Mapping", Arrhythmology Journal, vol. 34, p. 32-37, 2003, with partial English translation and English abstract.
Titomir, L. I, et al., "3.3 Cardioelectric potential mapping on a standard spherical image surface," Noninvasive Electrocardiotopography, p. 97-111, 2003, with English translation.
Shakin, V.V., "Computational Electrocardiography", p. 64-65, 1981, with partial English translation.
Golnik, E. R., et al., "Construction and Application of Preprocessor for Generation, Performance Control, and Optimization of Triangulation Grids of Contact Systems", Informational Technology, Voronezh State Technical University, No. 4, pp. 1-25, 2004, with partial English translation.
McLeod, R., et al., "Recent Progress in Inverse Problems in Electrocardiology", Nora Eccles Harrison Cardiovascular Research and Training Institute, University of Utah, pp. 1-20, 1998, in English.

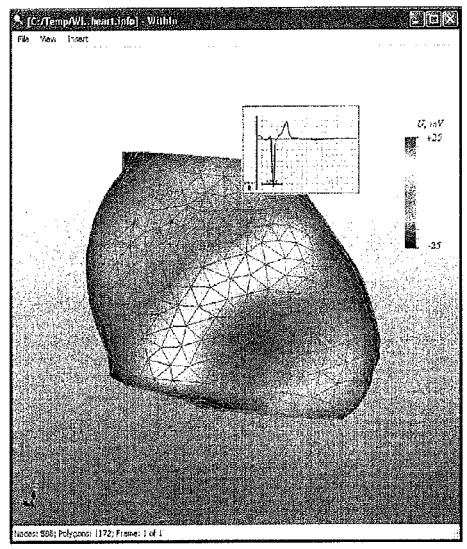 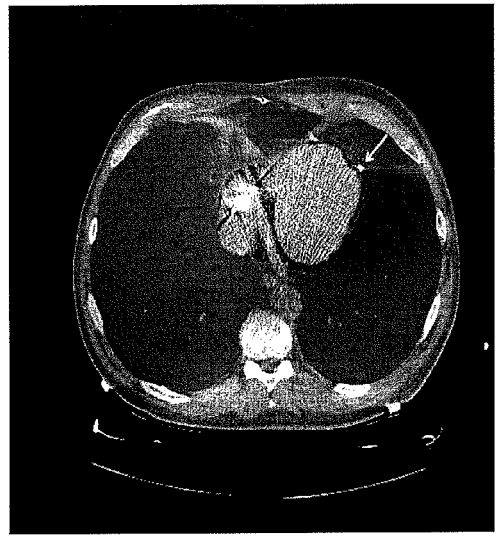
Fig. 16A    Fig. 16B
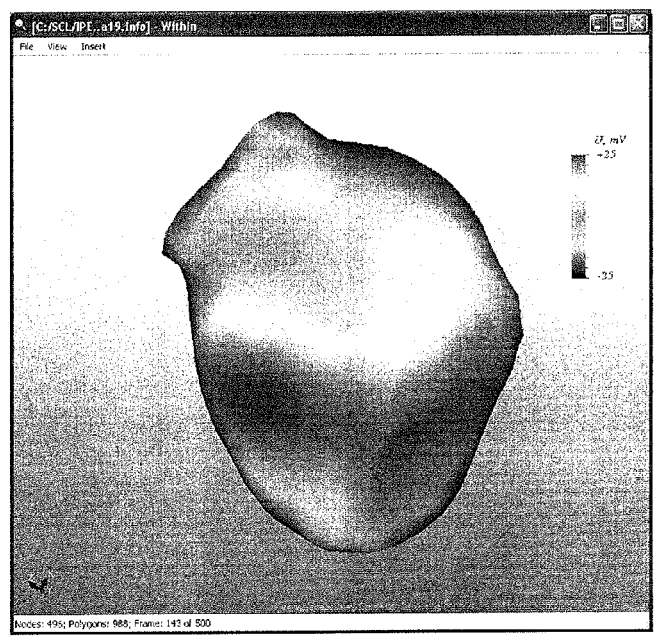
Fig. 16C

METHOD OF NONINVASIVE ELECTROPHYSIOLOGICAL STUDY OF THE HEART

FIELD OF THE INVENTION

The invention relates to medicine, namely to cardiology, cardiovascular surgery and functional diagnosis (clinical physiology), and is intended for performing a diagnosis procedure such as noninvasive electrophysiological study of the heart. More specifically, the invention is intended for reconstructing the dynamics of the heart electric field at internal points of the chest and, in particular, for obtaining intraesophageal and epicardial electrograms as well as for performing an activation epicardial mapping, namely for obtaining epicardial isopotential and isochronous maps (myocardium activation patterns) by a noninvasive way, i.e., without inserting registration devices into heart chambers, pericardial cavity, esophageal cavity, etc.

BACKGROUND OF THE INVENTION

The most common method for diagnosis of cardiac electrophysiological processes routinely used in clinical practice is electrocardiography in 12 standard leads. Simplicity and low cost of a standard electrocardiographical study together with its relatively high informativity have lead to its extremely widespread use in the daily practice.

However, electrocardiographical method has principled limitations. Activity of certain myocardium compartments is inadequately reflected in electrocardiographical signals registered in standard leads. As an example, one may name difficulties in ECG-diagnosis of myocardial infarction of back-basal compartments of the left ventricle. Furthermore, according to the superposition principle of electrodynamics, any electrocardiogram is the sum of electric potentials coming from sources at a great number of myocardium points. Since electrophysiological processes in different areas of the cardiac muscle proceed simultaneously, it is rather difficult to determine a local electric activity of the myocardium on standard ECG-leads. For example, an atrial re-polarization wave in humans in conditions of a normal cardiac rhythm is not revealed in ECG, as it is "hidden" by a high-amplitude QRS-complex reflecting a ventricular depolarization. A vector-electrocardiography method is characterized by the same limitations.

Greater possibilities are provided by a method for surface electrocardiographical mapping of the chest. The method consists in a synchronic registration of multiple (from 40 to 250 and more) unipolar ECG-leads from the chest surface and in constructing maps of the electric potential distribution over the chest surface by interpolation for each discrete moment of the cardiocycle.

However, this method does not allow one to determine more precisely a local electric activity of the myocardium. If an electrode is located on the chest surface, contributions to ECG-signal from the nearest and most remote, regarding a registration electrode, segments of the myocardium differ from each other by approximately one order. For an electrode placed on the heart surface, this difference is three orders. In this connection, for revealing a local electric activity of the heart, methods of invasive ECG-registration are used with an attempt to bring electrodes closely to the heart surface as much as possible.

Transesophageal electrophysiological study of the heart is based on inserting a probe with registration electrodes into the esophagus cavity. The esophagus at its certain part adjoins close enough to posterior wall of the left atrium and to posterior wall of the left ventricle; therefore, intraesophageal ECG-signals selectively register the activity of these heart compartments. Intraesophageal electrocardiography is applied, in particular, for differential diagnosis of supraventricular and ventricular arrhythmias (Transesophageal electrostimulation of the heart (Under edit Sulimov V. A., Makolkin V. I.). Moscow: Meditsina, 2001.-208 pp. [in Russian]).

However, methods above-mentioned permit one to reveal a local electric activity only of individual structures of the heart.

For a complex evaluation of cardiac electrophysiological processes and topical diagnosis of cardiac rhythm disturbances, an invasive electrophysiological study of the heart based on the direct registration of a set of electrograms from epicardial or endocardial surface of the heart is carried out. Methods indicated may be applied on "open-heart" in conditions of thoracotomy, as well as on the basis of intervention technologies for inserting registration devices (catheters) into cardiac cavities by transvascular access or into pericardial cavity by its fluoroscopically-guided transskin puncture.

Up-to-date realizations of methods afore-said are directed to a precise determination of three-dimensional (3-D) coordinates of registration electrodes by non-fluoroscopic techniques and to a visualization of results in the form of isopotential and isochronous maps on heart compartment models with means of computer graphics. Computer models of heart compartments are constructed on a great number of electrogram-registration points with known coordinates, as well as on the basis of CT or MRT data of the heart (Revishvili A. Sh., Rzaev F. G., Djetybaeva S. K. Electrophysiological diagnosis and intervention treatment of complicated forms of heart rhythm disturbances with using a system of three-dimensional electro-anatomical mapping.—Vestn. Aritmol. 2004, 34: 32-37 [in Russian]; Pokushalov E. A., Turov Shugaev P. L., Artemenko S. L. Radiofrequency ablation of ventricular tachycardia by transpericardial approach.—Vestn. Aritmol. 2006, 44: 58-62 [in Russian]).

To this group, methods for non-contact endocardial mapping based on inserting a "swimming" balloon catheter into cardiac cavities, registering a set of electrograms on the heart surface and reconstructing endocardial electrograms by computational way on obtained data are also related. (Schilling R. J., Kadish A. H., Peters N. S. et al. Endocardial mapping of atrial fibrillation in the human right atrium using a non-contact catheter.—European Heart Journal. 2000, 21: 550-564).

A disadvantage of above-disclosed methods that is eliminated in the present invention consists in their invasive character.

Analogues of the present invention are methods for reconstructing electrograms at internal points of the chest by computational way on data of synchronic registering a set of ECGs on the chest surface.

These methods are based on solution of the inverse problem of electrocardiography. Statement of the inverse problem of electrocardiography (IP ECG) is formulated in works of Barr D., Spach M Solutions of the inverse problem directly expressed in terms of potentials//Theoretical fundamentals of electrocardiology [Russian translation under edit. Nelson K. V. and Geselovitz D. V.]—Moscow: Meditsina 1979, pp. 341-352; MacLeod R. S., Brooks D. H. Recent progress in the inverse problem in electrocardiology//IEEE Eng. in Med. Bio. Mag. 17:1, pp. 78-83, January 1998; Rudy Y., Messinger-Rapport B. J. The inverse problem in electrocardiography: Solutions in terms of epicardial potentials. CRC Crit. Rev. Biomed. Eng. 1988, 16: 216-268.

From the mathematical standpoint, IP ECG is a problem of harmonic continuation (propagation) of the potential in the direction of sources, i.e., the Cauchy problem for the Laplace equation. Computational domain, in which the Laplace equation is given, represents a part of the chest bounded by heart's external surface, chest surface on which ECG-registration is accessible, and by imaginary cross-sections of the chest at the level of the diaphragm and clavicles.

At the part of the chest surface where ECG-registration is accessible, values of the electric potential obtained as a result of ECG-mapping, as well as the condition of equality-to-zero of a potential normal derivative are given. These data compose the Cauchy conditions.

The Cauchy problem consists in finding the electric field potential in domain indicated and its trace on the heart surface and on cross-sections of the chest in such a way that the potential in computational domain would satisfy the Laplace equation, while on the torso surface where ECG-registration is accessible it would satisfy the Cauchy conditions.

According to Hadamard, the Cauchy problem for the Laplace equation is ill-posed, as any negligible errors in the condition may result in arbitrary large errors in the solution. For solving the Cauchy problem for the Laplace equation, it is necessary to apply special so-called regularizing algorithms of solution (Denisov A. M. Introduction to the theory of inverse problems [in Russian].—Moscow: Moscow State University, 1994; Tikhonov A. N., Arsenin V. Ya. Methods for solution of incorrect problems [in Russian].—Moscow: Nauka, 1986, 312 pp.).

To solve the Cauchy problem for the Laplace equation in the above-disclosed statement (the inverse problem of electrocardiography) by an analytical way appears to be impossible. Therefore, the inverse problem of electrocardiography is numerically solved by means of computational mathematics with using computer techniques.

One of the ways for solving the inverse problem of electrocardiography is a method for reconstructing the electric field on "quasi-epicard", i.e., on a conditional spherical surface surrounding the heart. From the mathematical standpoint, this method is based on representation of the heart electric field potential in the form of a harmonic polynomial (sphere function), whose coefficients are found from the condition of equality (or the minimum of mean square deviation) of polynomial values and values of an ECG-signal at points of its registration with taking into account the equality-to-zero of a potential normal derivative on the chest surface. For providing the stability of solution, a polynomial of degree not higher than 4 is used. An essential disadvantage of this method is that, when the radius of sphere diminishes, i.e., as "quasi-epicard" surface approximates to a real surface of the heart, the accuracy of potential reconstructing sharply drops. When "quasi-epicard" surface approximates to the chest surface, the resolution of the method in terms of revealing a local electric activity of the myocardium decreases (Titomir L. I., Kneppo P. Mathematical modeling of heart's bioelectric generator.—Moscow: Nauka, Physmathlit, 1999.-448 pp. [in Russian]; Titomir L. I., Trunov V. G., Aidu E. A. I. Noninvasive electrocardiography.—Moscow: Nauka, 2003.-198 pp. [in Russian]).

For solving boundary problems for the Laplace equation, methods of integral equations of the potential theory, more known in English-written literature as boundary element methods, are widely used (Brebbia C., Telles J., Wrobel L. Boundary element methods [Russian translation].—Moscow, Mir, 1987). The present approach to IP ECG solution is proposed in works of Taccardi E., Plonzi R., Barr R. (Barr R., Spach M Inverse problem solutions directly expressed in terms of a potential//Theoretical fundamentals of electrocardiography [Russian translation]. Above-mentioned methods suppose, in particular, the representation of heart and torso surfaces as polygonal surfaces, i.e., splitting boundary surfaces into a great number of triangular elements. According to the boundary element method, IP ECG for a homogeneous model of the chest is reduced to solving a system of two Fredholm integral equations of $1^{st}$ and $2^{nd}$ kinds, which is approximately substituted by a system of matrix-vector equations:

$$A_{11}x + A_{12}y = c_1$$

$$A_{21}x + A_{22}y = c_2' \quad (1)$$

where $A_{i,j}$ are known matrices, $x_1$, $x_2$ are unknown vectors having a sense of sought-for values of the potential and its normal derivatives in nodes of triangulation grids approximating the heart surface and torso cross-section surfaces, $c_1$, $c_2$ are known vectors calculated on known data of the problem.

In the method for noninvasive epicardial mapping suggested by Shakin V. V. et al. the following algorithm of IP ECG solution was used.

The system of matrix-vector equations (1) by means of elementary transformations was reduced to a system of linear algebraic equations (SLAE) to be resolved in explicit form:

$$\Phi_H = Z_{HB} \cdot \Phi_B, \quad (2)$$

where $\Phi_H$ is an unknown vector having a sense of sought-for values of the potential in nodes of triangulation grids approximating the heart surface and torso cross-section surfaces, $Z_{HB}$ is a known matrix, $\Phi_B$ is a known vector. For calculating matrix $Z_{HB}$, it is necessary to use an inversion procedure of matrices entering the system (1), one of matrices to be inversed being non-square and bad-conditioned. For implementation of this procedure, constructing a Moore-Penrose pseudo-inverse matrix on the basis of SVD-decomposition of an initial matrix and substituting small singular numbers by zeroes were performed.

The heart and torso surfaces were represented as simplified models in the form of cylindrical and ellipsoidal surfaces to be constructed on the basis of two-projection roentgenography of the chest. Results of mapping in the form of isopotential and isochronous maps were imposed upon model scanned-schemes of heart compartments. This methodology was used for revealing a localization of additional pathways (APW) at manifested WPW syndrome and ectopic sources at ventricular extrasystole (Shakin V. V. Computational electrocardiography [in Russian].—Moscow: Nauka, 1980).

In his works, Shakin V. V. has emphasized a promising outlook of the application of computed tomography techniques for more precise constructing the torso and heart surfaces; however, this approach could not be used because of unsatisfactory development of methods for computer tomography of the heart.

The most similar to a method claimed here (prototype) is the methodology of noninvasive electrocardiographical imaging (ECGI).

In this methodology, a surface mapping is realized with using 240 unipolar electrodes placed in a special vest to be put on a patient for a study period. The torso and heart surfaces are determined based on computer (CT) or MRT tomography of the chest. A reconstruction algorithm is based on solution of the inverse problem of electrocardiography by the boundary element method.

The heart and torso surfaces are approximately represented as polygonal surfaces. For solving IP ECG, the system of matrix-vector equations (1) is also used, which by elementary transformations is reduced to a system of linear algebraic equations $$Ax=c \qquad (3)$$

where x is an unknown vector having a sense of sought-for values of the potential in nodes of triangulation grids approximating the heart surface and torso cross-section surfaces, A is a known matrix, c is a known vector.

The system of linear algebraic equations (3) is bad-conditioned. For its solving the Tikhonov regularization method and the iteration regularization method based on GMRes-algorithm are used. The Tikhonov method is based on solution of the following system instead of the system (3)

$$(A^T \cdot A + \alpha E)x = A^T c$$

where $A^T$ is a matrix transponated with respect to matrix A, E is a unit matrix, $\alpha$ is a regularization parameter (a small positive real number).

The iteration regularization method is based on solution of the system (3) by a method of sequential approximations with restricting a number of iterations on the basis of GMRes-algorithm; this method belongs to a group of Krylov subspace methods (Ramanathan C., Ghanem R. N., Jia P., Ryu K., Rudy Y. Electrocardiographic Imaging (ECGI): A Noninvasive Imaging Modality for Cardiac Electrophysiology and Arrhythmia//Nature Medicine, 2004; 10:422-428; Rudy Y., Ramanathan C., Ghanem R. N., Jia P. System and method for noninvasive electrocardiographic imaging (ECGI) using generalized minimum residual (GMRes)//U.S. Pat. No. 7,016, 719 B2, 2006).

The similar technique was used in works of Berger T., Fisher G., Pfeifer B. et al. Single-Beat Noninvasive Imaging of Cardiac Electrophysiology of Ventricular Pre-Excitation// J. Am. Coll. Cardiol., 2006; 48: 2045-2052).

This technique was applied for reveling a APW-localization at manifested WPW syndrome, ectopic sources at ventricular extrasystole and tachycardia, reconstruction of the dynamics of the myocardium activation at atrium flutter.

An essential disadvantage of the method under consideration is the use of a chest model with a constant coefficient of specific electroconductivity. Specific electroconductivity of different organs and tissues of the chest is considerably differed. A variable coefficient of electroconductivity of biological tissues rather greatly influences the heart electric field in the chest, what confirm the data of experimental research (Rudy Y., Wood R., Plonsey R., Liebman J. The effect of high lung conductivity on electrocardiographic potentials. Results from human subjects undergoing bronchopulmonary lavage// Circulation 1982; 65: 440-445). The greatest role plays the difference in electroconductivity between lungs and surrounding soft tissues (at 4-5 times). Potentials of the heart electric field of model sources calculated for homogeneous and inhomogeneous models of the chest differ from each other by 15%-20% (Titomir L. I., Kneppo P. Mathematical modeling of heart's bioelectric generator.—Moscow: Nauka, Physmathlit, 1999.-448 pp. [in Russian]. Thus, neglect of an electrical inhomogeneity of chest tissues may lead to greater errors of reconstructing the heart electric field.

The present invention is aimed at improving the accuracy of noninvasive electrophysiological study of the heart at the expense of taking into account a different electroconductivity coefficient of chest tissues.

SUMMARY OF THE INVENTION

For carrying out an electrophysiological study of the heart, a registration of a set of electrograms from the heart surface is necessary based on which isopotential, isochronous maps are constructed and electrophysiological processes in the cardiac muscle are diagnosed. In order to obtain these electrograms, an invasive way is used, i.e., insertion of special registration devices into heart chambers or pericardial cavity.

The present invention consists in reconstructing electrograms, whose experimental registration requires an invasive access, by computational way on unipolar ECG recorded at 80 and more points of the chest surface. Based on a set of surface electrocardiograms for each discrete moment of the cardiocycle, values of the heart electric field potential at points of ECG-recording are determined and, by interpolation, a value of the electric field potential at each point of the chest surface is calculated. On data of any visualization methodology (computer tomography, magneto-resonance tomography), boundaries of the chest surface and heart epicardial surface, as well as values of specific electroconductivity of a tissue at each point of the chest are determined.

Further, a continuation of the electric field potential throughout the whole surface of the chest up to the heart epicardial surface is implemented by computational way on the basis of solution of the Cauchy problem for the Laplace equation in an inhomogeneous medium. Solution of the Cauchy problem for the Laplace equation is reduced to a numerical solution of an operator equation of $1^{st}$ kind in the space $L_2$. Solution of this operator equation is realized by solution of the equivalent problem of minimization of a convex positive quadratic functional. The variation problem indicated is solved by numerical minimization on the basis of gradient methods or by numerical solution of the Euler equation. All these methods have an iteration character. At each step of an iteration procedure, solution of mixed boundary problems for Laplace equation in an inhomogeneous medium is performed by the finite element method. Regularization in computational procedures is provided at the expense of limiting a number of iterations or of using the Tikhonov method. Regularization parameters are determined according to the principle of the residual.

The above-written sequence of procedures is repeated for each discrete moment of the cardiocycle. On obtained values of the potential at given internal points of the chest, required electrograms are reconstructed by interpolation. Based on reconstructed electrograms, isopotential, isochronous maps on realistic models of the heart are constructed, the dynamics of the myocardium excitation is reconstructed and diagnosis of electrophysiological processes in the cardiac muscle is performed.

BRIEF DESCRIPTION OF FIGURES

FIG. 5 (continued). In upper drawing an isoline drift is shown, in lower one—a resulting filtered signal.

DETAILED DESCRIPTION OF PREFERRED EMBODIMENTS

To provide a comprehensive understanding of the invention, its specific illustrative embodiments are described below; however, those of ordinary skill in the art will recognize that methods and systems may be modified within the scope of the invention as defined by the appended claims.

Methods and systems disclosed here use a device of surface ECG mapping, visualization techniques of computer (CT) or magneto-resonance (MRT) tomography, computing techniques, as well as mathematical algorithms of solution of the inverse problem of electrocardiography for non-invasive reconstructing electrograms at internal points of the chest and on the heart epicardial surface and for constructing isopotential and isochronous epicardial maps on a realistic three-dimensional (3-D) computer model of the heart.

Figure 1:
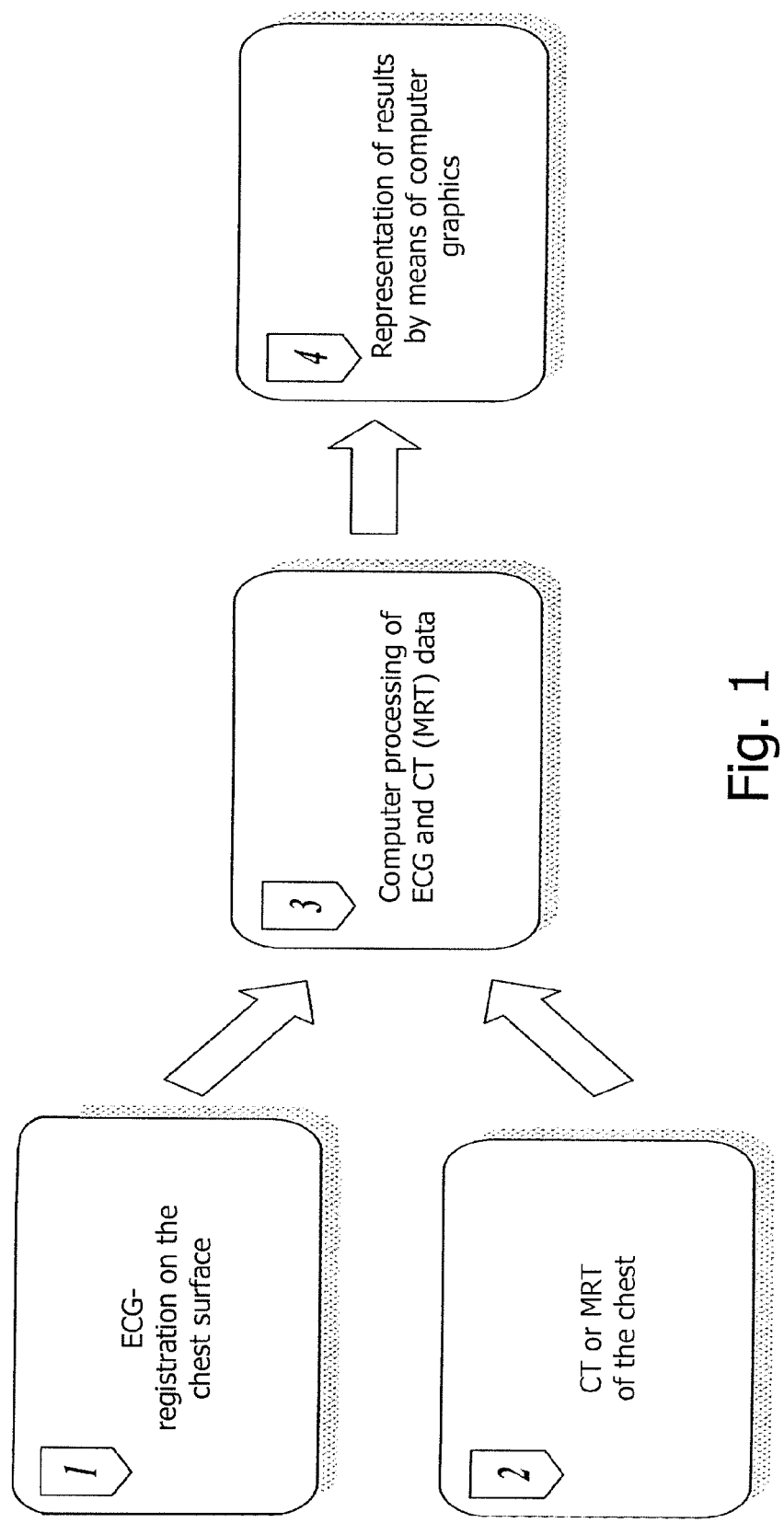
FIG. 1 illustrates a general scheme of the method.

FIG. 1 illustrates a general schematic view of the method. The method includes (1) a registration of 240 unipolar ECG on the chest surface, (2) an implementation of CT or MRT of the chest, (3) data processing of surface ECG mapping and of computer (MRT) tomography using computing techniques and (4) a representation of the obtained electrophysiological information with means of computer graphics.

Figure 2:
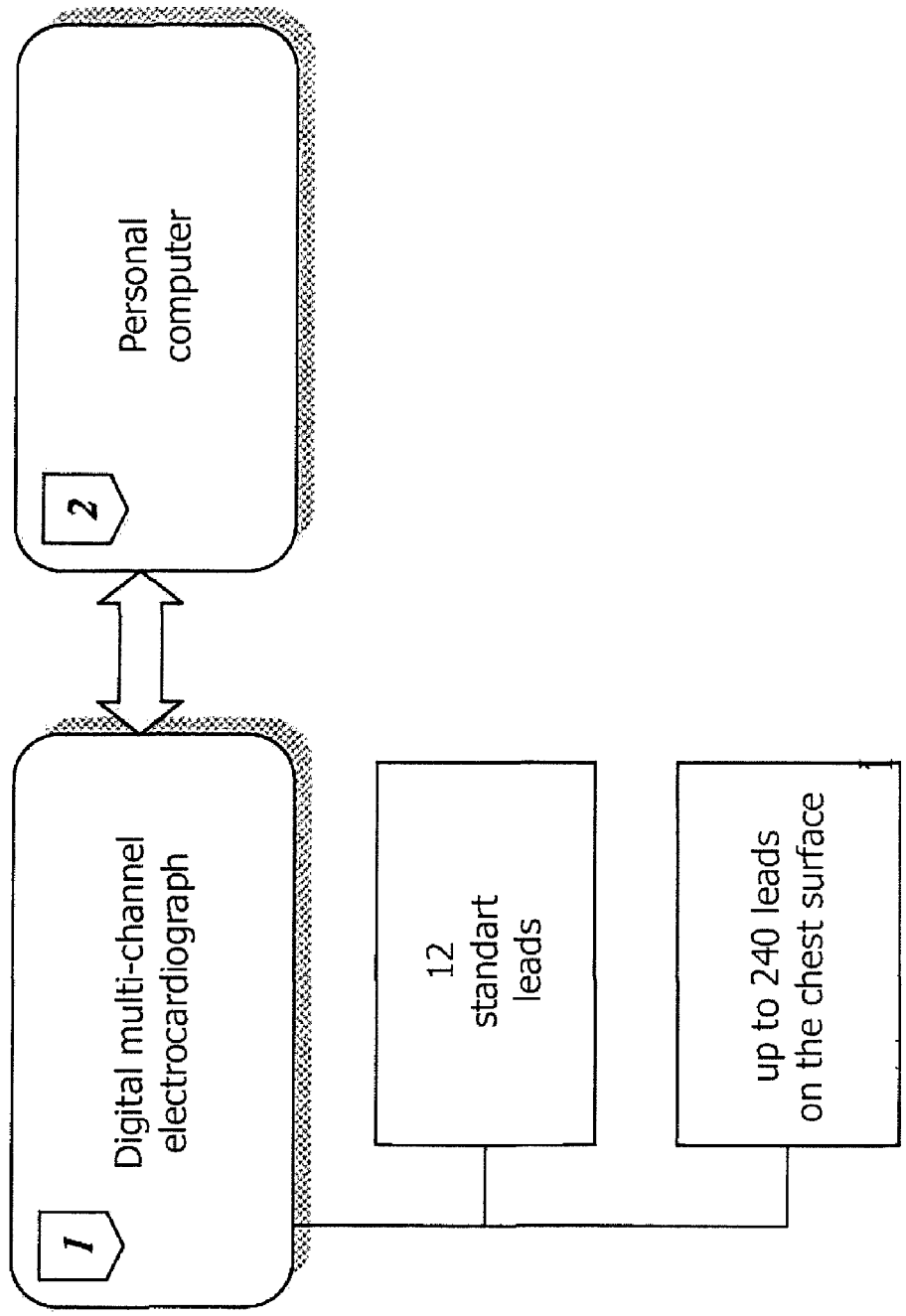
FIG. 2 shows a schematic view of the methodology of surface ECG mapping.

FIG. 2 illustrates a schematic view of the methodology of surface ECG mapping. A mapping device comprises a digital multi-channel electrocardiograph (1) connected with a personal computer (2). The digital multi-channel electrocardiograph allows one to register ECG-signals in 12 standard leads and in up to 240 unipolar leads from the chest surface.

Figure 3:
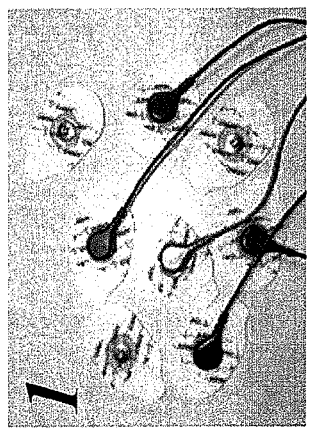
FIG. 3 illustrates a scheme of imposing electrodes on the chest surface.
Figure 3:
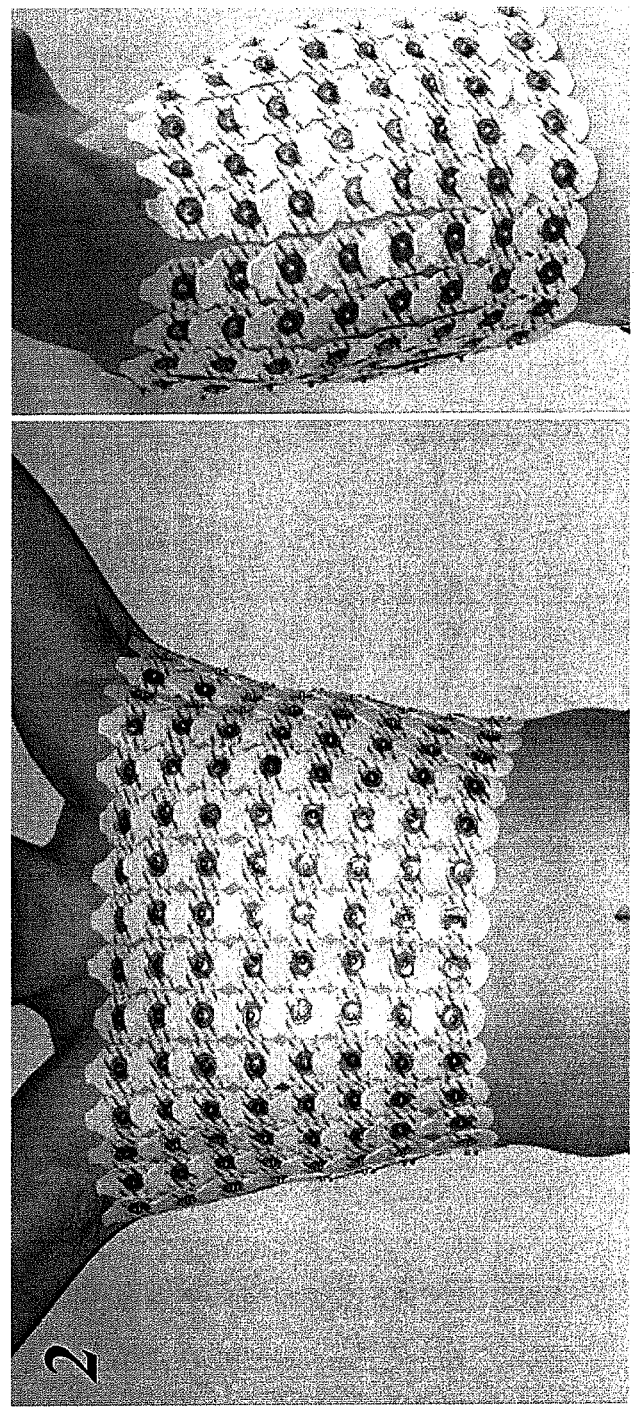

FIG. 3 illustrates a scheme of imposing electrodes. For surface ECG mapping, one-off chlorine-silver electrodes are used (1). Electrodes are imposed in the form of 5-8 horizontal strips (belts) positioned at similar distances along the vertical. The upper strip is positioned at the level of sterno-cleidal articulation, the lower strip—at the level of lower edge of rib-arch. Each strip includes from 16 to 30 electrodes placed at similar distances in circumference of the chest (2). When a roentgen computer tomography is used as a visualization methodology, one-off metal chlorine-silver electrodes are applied as they are well visualized in roentgen tomography images and give a minimum level of artifacts. When a magneto-resonance therapy is used as a visualization methodology, one-off graphite electrodes are applied as they show the similar properties for this tomography technique.

Figure 4:
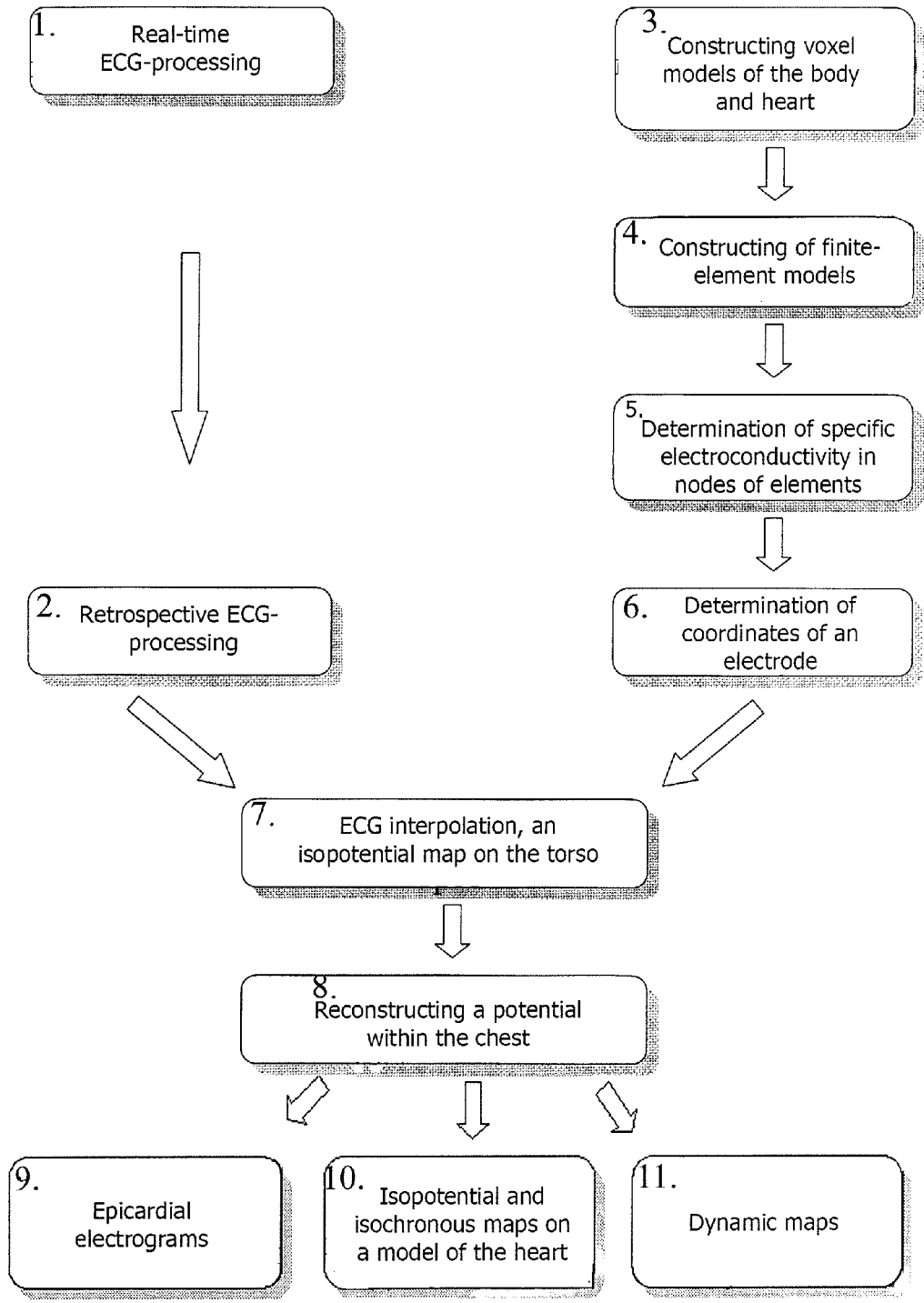
FIG. 4 presents the main stages of computer processing of the information.

FIG. 4 depicts the main stages of computer processing of the information.

The stage (1) is a real-time processing of ECG-signals in the course of multi-channel ECG registration from the chest surface. The stage (2) is a retrospective processing of ECG-signals. The stage (3) includes constructing voxel models of the chest, heart and its compartments on CT or MRT data. The stage (4) comprises constructing polygonal surfaces of the chest, heart and its compartments. The stage (5) includes an automatic determination of coordinates of registration electrodes on the chest surface according to CT or MRT data. At stage (6) a surface interpolation of values of surface mapping ECG-signals at each discrete moment and a construction of isopotential maps on the chest surface are performed. The stage (7) includes a computational reconstruction of the heart electric field potential at internal points of the chest and on the heart epicardial surface. At the last stage, reconstructing epicardial electrograms (8) and constructing epicardial isopotential, isochronous maps with using means of computer graphics (9) on a realistic computer model of the heart, and visualizing the dynamics of electrophysiological processes of the myocardium in animation mode (propagation mapping) (10) are performed, respectively.

Figure 5:
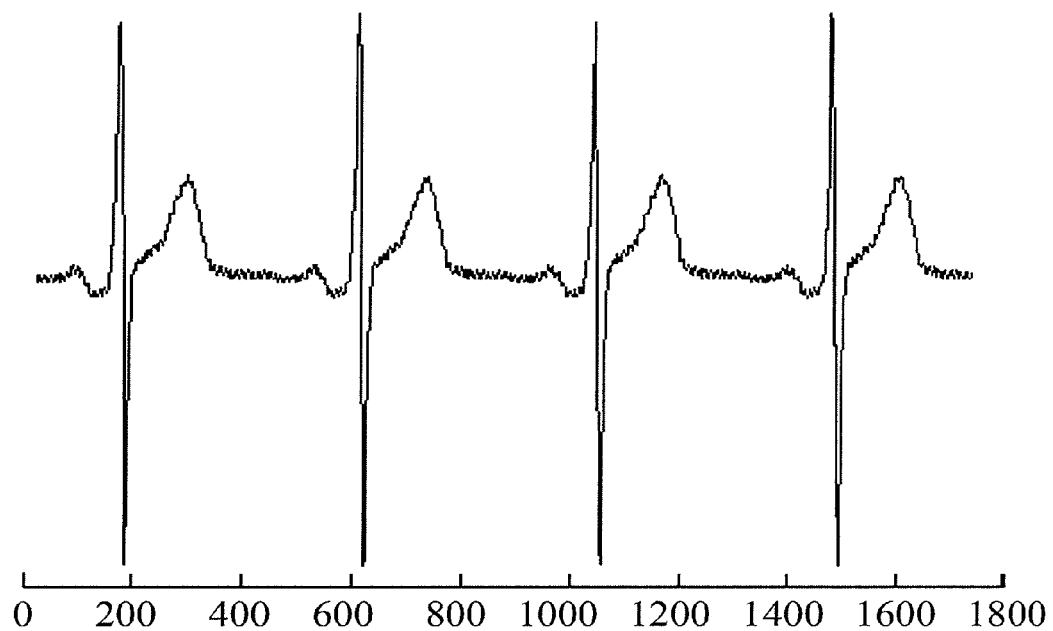
FIG. 5 illustrates processing of ECG-signals in the course of ECG mapping in real-time mode. In upper drawing, power-line noises are shown, in lower one—muscle noises.
Figure 5:
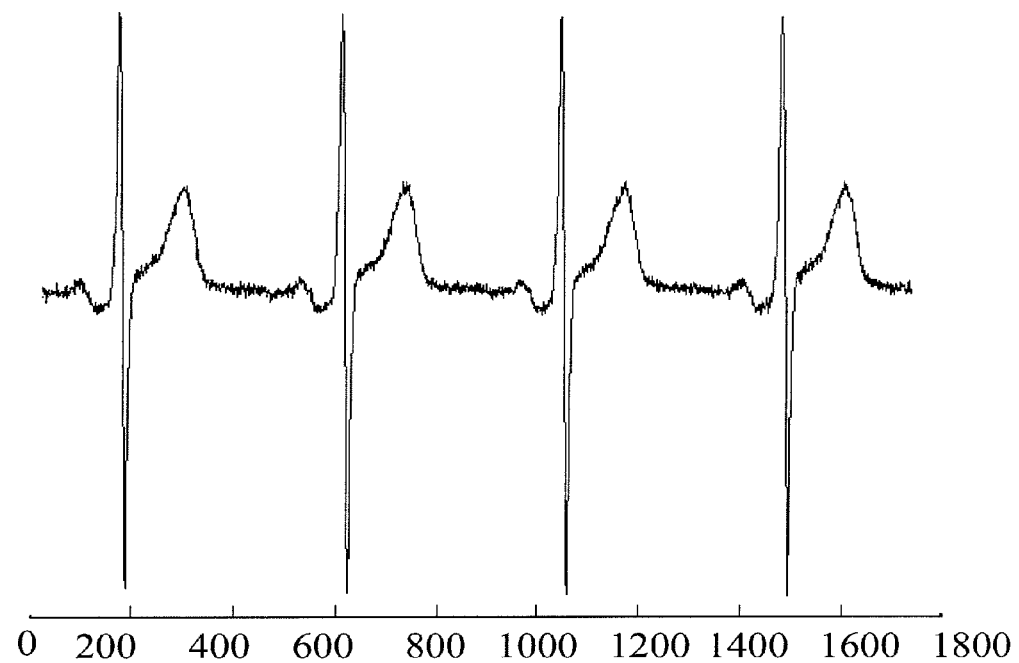
Figure 5:
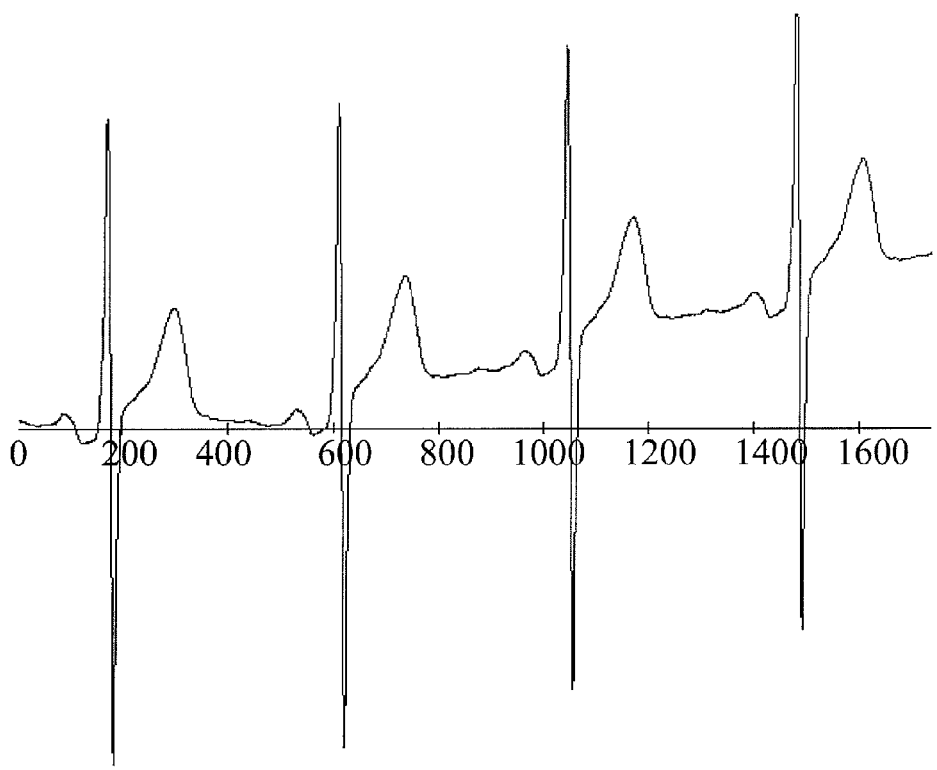
Figure 5:
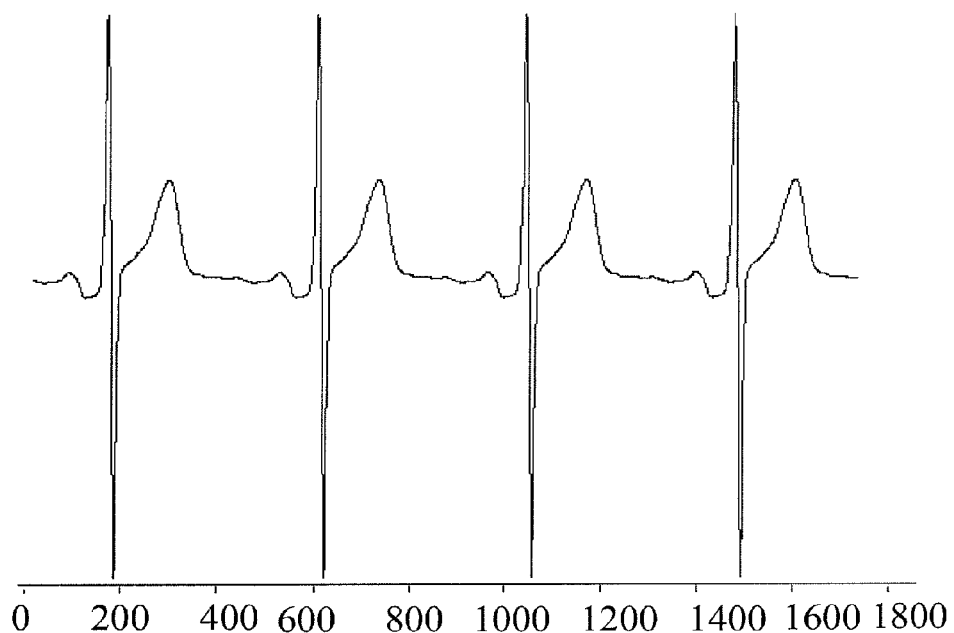

FIG. 5 illustrates processing of ECG-signals in the course of real-time ECG mapping. ECG-signals registered are reflected in computer display. An operator controls the quality of an ECG-signal in each of the leads; if necessary, a programmed suppression of power-line (1) и muscle (2) noises and of isoline drift (3) is used. Automatic control of the contact of an electrode with skin and correctness of imposing electrodes based on spectral and mutual-correlation analyses of ECG-signals are also performed. A result of stage (1) represents digitalized and filtered values of ECG-signals in 240 unipolar leads from the chest surface and in 12 standard leads with duration up to 3 minutes.

Figure 6:
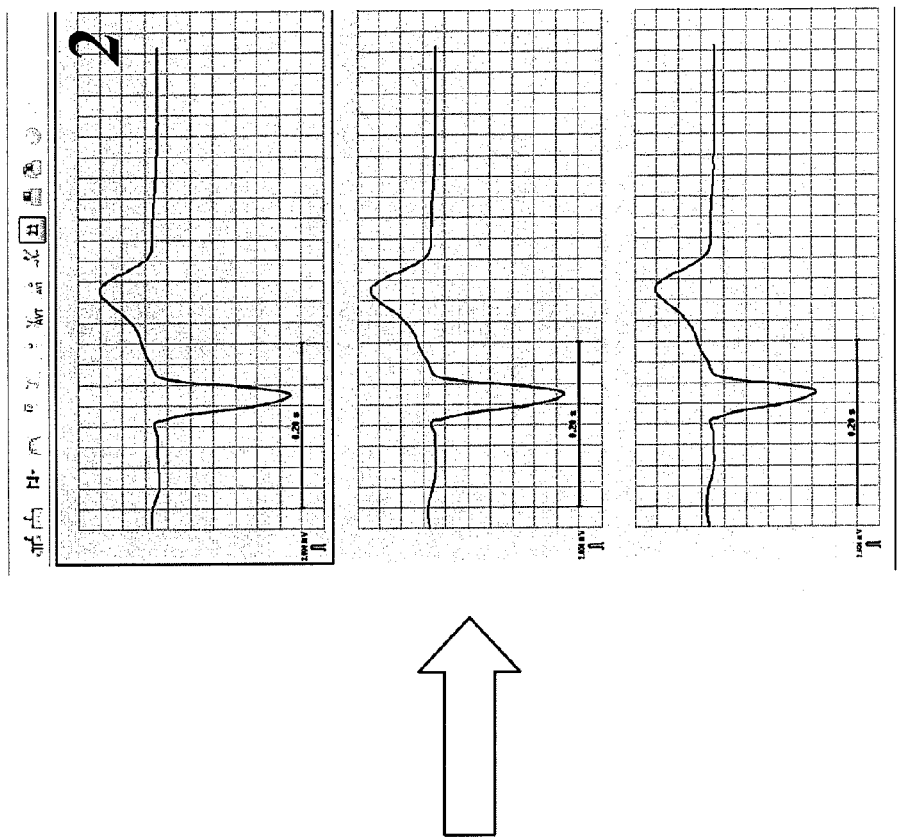
FIG. 6 illustrates a retrospective processing of ECG-signals.
Figure 6:
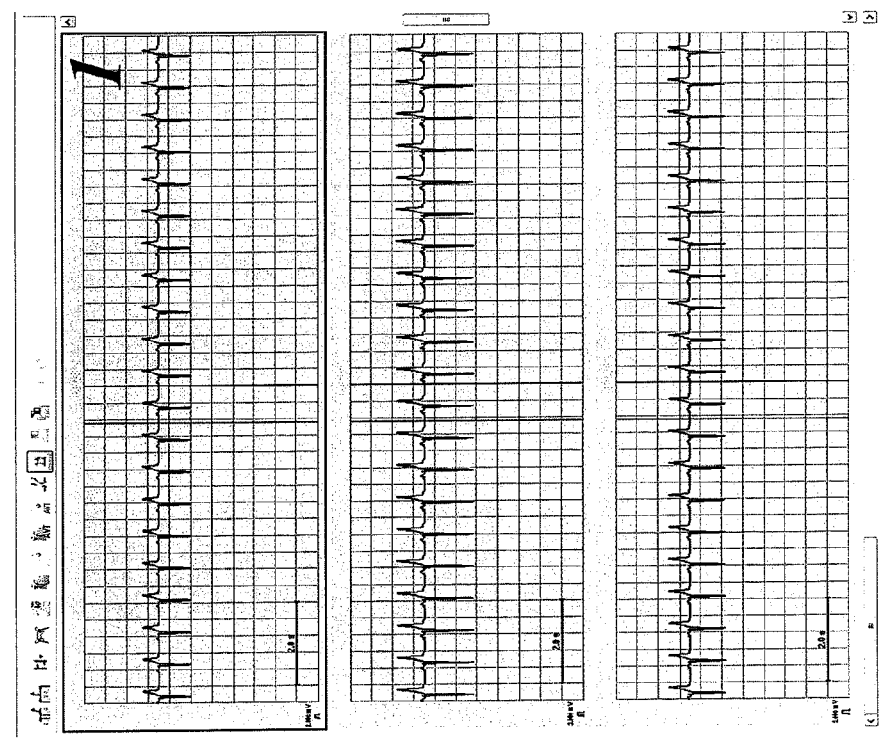
Figure 6:
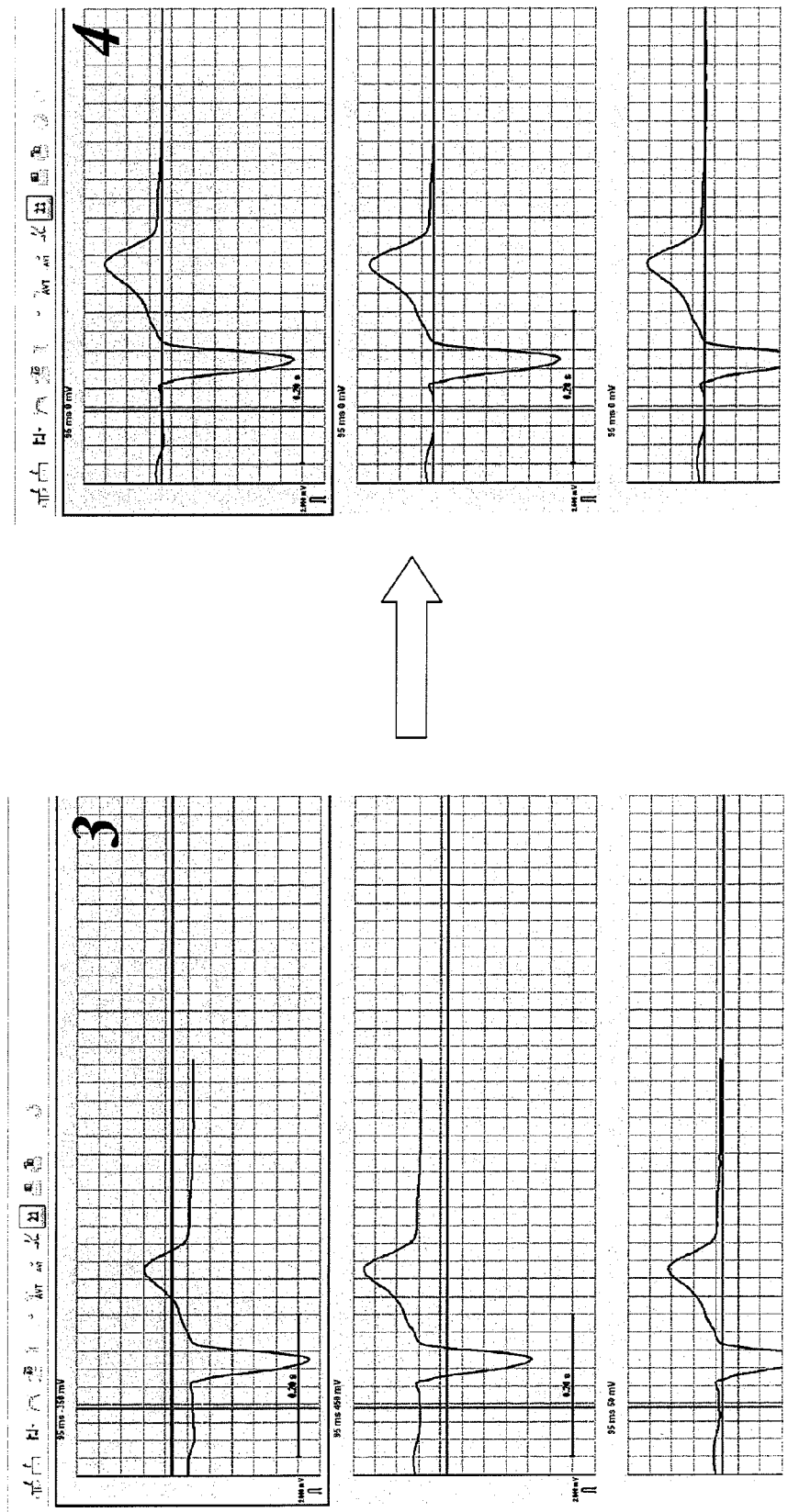

FIG. 6 depicts a retrospective processing of ECG-signals.

An operator looks through ECG-signals registered and selects one or several cardiocycles (1, 2) for posterior processing. Further, a reduction of ECG to a unity isoline (3, 4) is implemented: to this end, operator selects in one of ECGs such a time interval τ within which an ECG-signal coincides with an isoline (as a rule, this interval belongs to the segment PQ). Correction of ECG-signals is performed according to the formula:

$$U_0(t)=U(t)-u_0,$$

where $U_0(t)$ is the corrigiert ECG-signal, $U(t)$ is an initial ECG-signal, $u_0$ is an average value of an initial ECG-signal at time interval τ.

Afterwards, operator selects a cardiocycle fragment, being under interest, for subsequent calculations.

Figure 7:
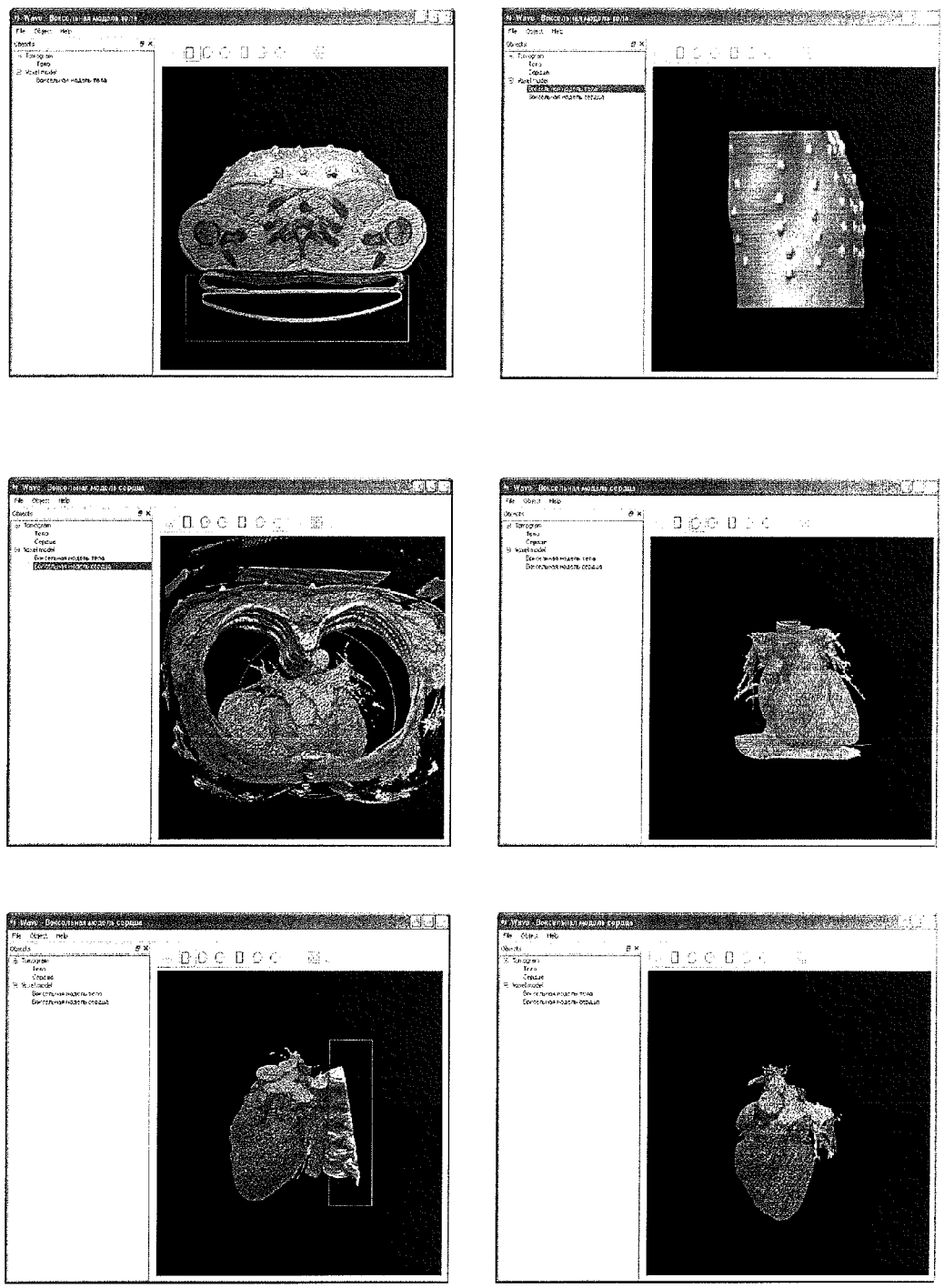
FIG. 7 shows constructing a voxel model of the torso and heart in voxel graphics editor.

FIG. 7 illustrates constructing a voxel model of the torso and heart in voxel graphics editor.

On CT or MRT data of the chest and heart, a voxel rendering of anatomical structures of the chest is carried out. To this end, a shear-warp factorization of the viewing transformation algorithm is used, which belongs to a group of scanline-order volume rendering methods.

The concept of the voxel rendering method applied here consists of three main steps (Philippe Lacroute Fast Volume Rendering Using a Shear-Warp Factorization of the Viewing Transformation.—Ph.D. dissertation, Technical Report CSL-TR-95-678, Stanford University, 1995).

At first step, volume data are transformed by a shear matrix in the corresponding object space, each parallel slice of volume data after transformations passing through a special filter for diminishing distortions.

At second step, an intermediate 2D image within the same shear space is formed from a combined set of filtered and sheared slices by their direct-order superposition.

At third step, the intermediate 2D image obtained is transferred in a normal image space with using a shear matrix, and further it again passes through a filter for formation of a final image.

An operator with the help of instruments of voxel edition makes ready a voxel model of the torso, heart or one of its structures.

Figure 8:
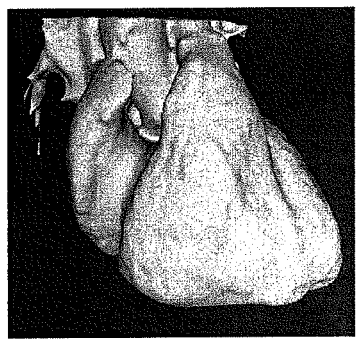
FIG. 8 illustrates constructing polygonal surfaces (triangulation grids) of the torso and heart and a finite-element grid on the basis of voxel models. In the left column, stages of constructing a polygonal grid of the heart are shown: an initial grid (350 000 elements), a reconstructed grid (20 000 elements), a rarefied grid (3 000 elements). In the right column, stages of constructing a polygonal grid of the torso are shown: an initial grid (900 000 elements), a reconstructed grid (20 000 elements), and a rarefied grid (3 000 elements).
Figure 8:
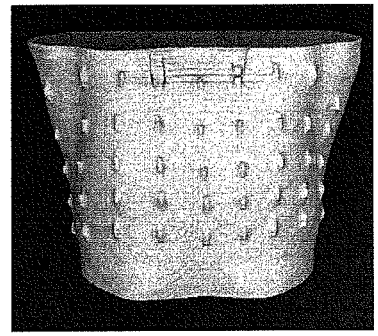
Figure 8:
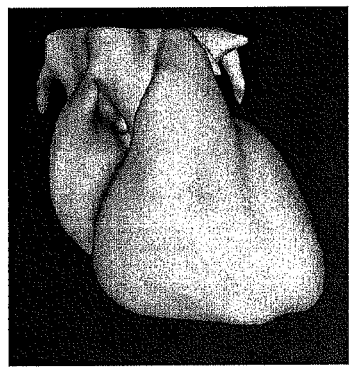
Figure 8:
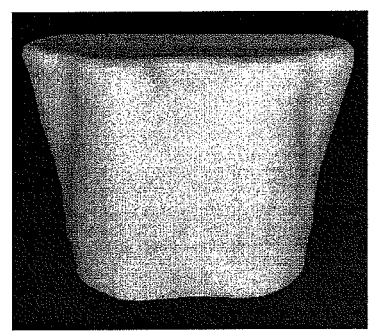
Figure 8:
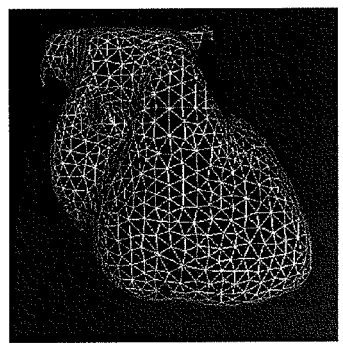
Figure 8:
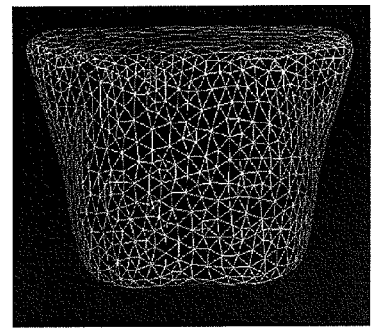
Figure 9:
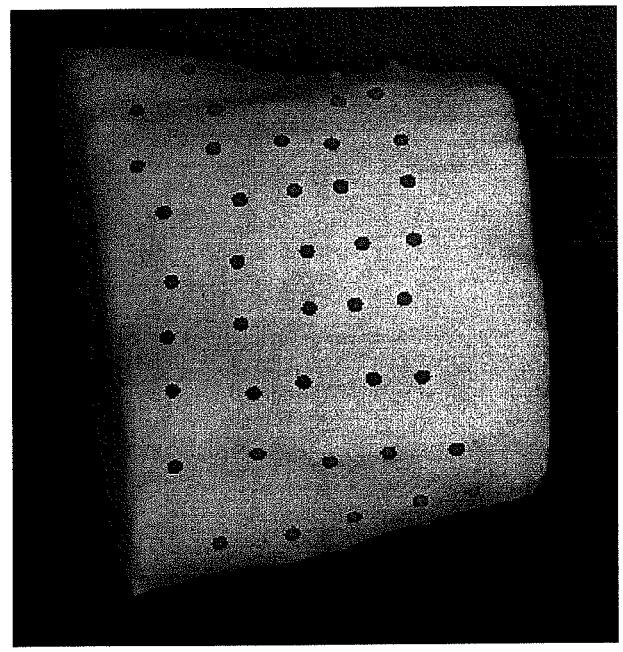
FIG. 9 shows an automatic determination of coordinates of electrodes on CT or MRT data of the chest.
Figure 9:
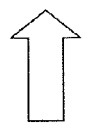
Figure 9:
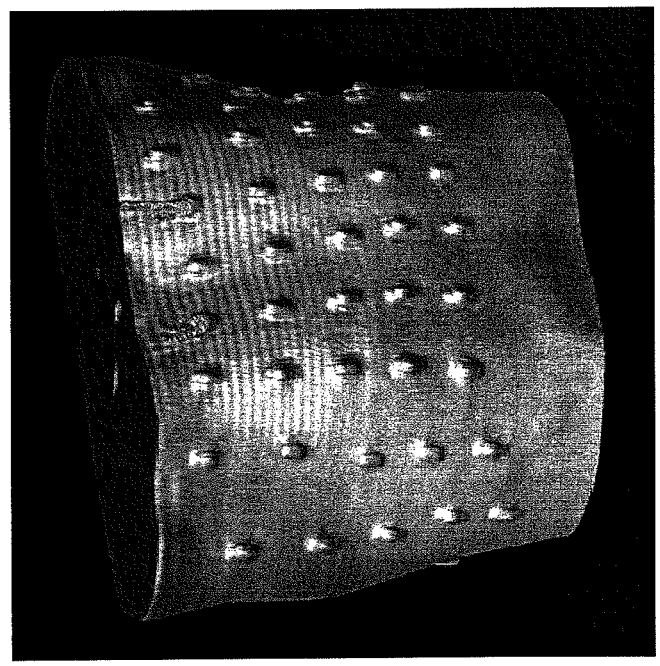

FIG. 8 illustrates constructing polygonal surfaces (triangulation grids) of the torso and heart on the basis on voxel models.

Based on the obtained voxel models, polygonal surfaces consisting of united planar triangles and volume tetrahedral finite-element meshes are automatically constructed.

Initial data represent a three-dimensional scalar field of densities in a voxel representation, i.e., a three-dimensional right-angled grid, in whose nodes values of conditional densities of chest tissues are given. Constructing triangulation grids of the torso and heart represents a construction of polygonal surfaces that by the nearest way repeat surfaces of aforesaid structures given by the definite level of density.

A procedure of constructing polygonal surfaces includes the following steps:
  filtrating initial voxel models for diminishing a casual noise level;
  constructing a finite-element volume and surface grid on the basis of the «exhaustion method», more known in English-written literature as an «advancing front» algorithm.

Advancing front algorithm is described in more detail in Lo S. H. Volume Discretization into Tetrahedra—II. 3D Triangulation by Advancing Front Approach//Computers and Structures, Pergamon, Vol. 39, No 5, p.p. 501-511, 1991; Rassineux A. Generation and Optimization of Tetrahedral Meshes by Advancing Front Technique//International Journal for Numerical Methods in Engineering, Wiley, Vol. 41, p.p. 651-674, 1998; Gol'nik E R., Vdovichenko A. A., Uspekhov A. A. Construction and Application of a Preprocessor of Generation, Quality Control, and Optimization of Triangulation Grids of Contact Systems//Information Technologies, 2004, No. 4, p. 2-10 [in Russian].

At the next step, a specific electroconductivity coefficient of a biological tissue is determined for each node of a finite-element grid. Firstly, a type of a biological tissue is determined based on Hounsfield numbers in computer tomograms or values of a MR-signal in magneto-resonance tomograms. Afterwards, a specific electroconductivity coefficient is ascribed to every type of a biological tissue on the basis of published data.

An example of conformity between Hounsfield numbers and specific electroconductivity values of chest tissues is given below (Hofer M. Computer tomography teaching manual [Russian translation]. Moscow: Meditsinskaya literatura, 2006; Martirosov E. G., Nikolaev D. V., Rudnev S. G. Technologies and methods for determination of human body composition. [In Russian].—Moscow: Nauka, 2006).

TABLE I

| Type of a tissue | Hounsfield number, NE | Average specific electroconductivity, S/m |
|---|---|---|
| Liquor | 15-25 | 1.53 |
| Blood (contrasted) | 150-250 | 0.67 |
| Skeletal muscles | 30-60 | 0.33 |
| Myocardium | 27-36 | 0.33 |
| Adipose tissue | −190 ÷ −30 | 0.067 |
| Liver | 46-73 | 0.25 |
| Skin | 70-100 | 0.18 |
| Lungs (at breath) | −800 ÷ −900 | 0.043 |
| Bone tissue, sponge | 250-300 | 0.0067 |
| Bone tissue, compact | 500-700 | 0.00025 |

Figure 10:
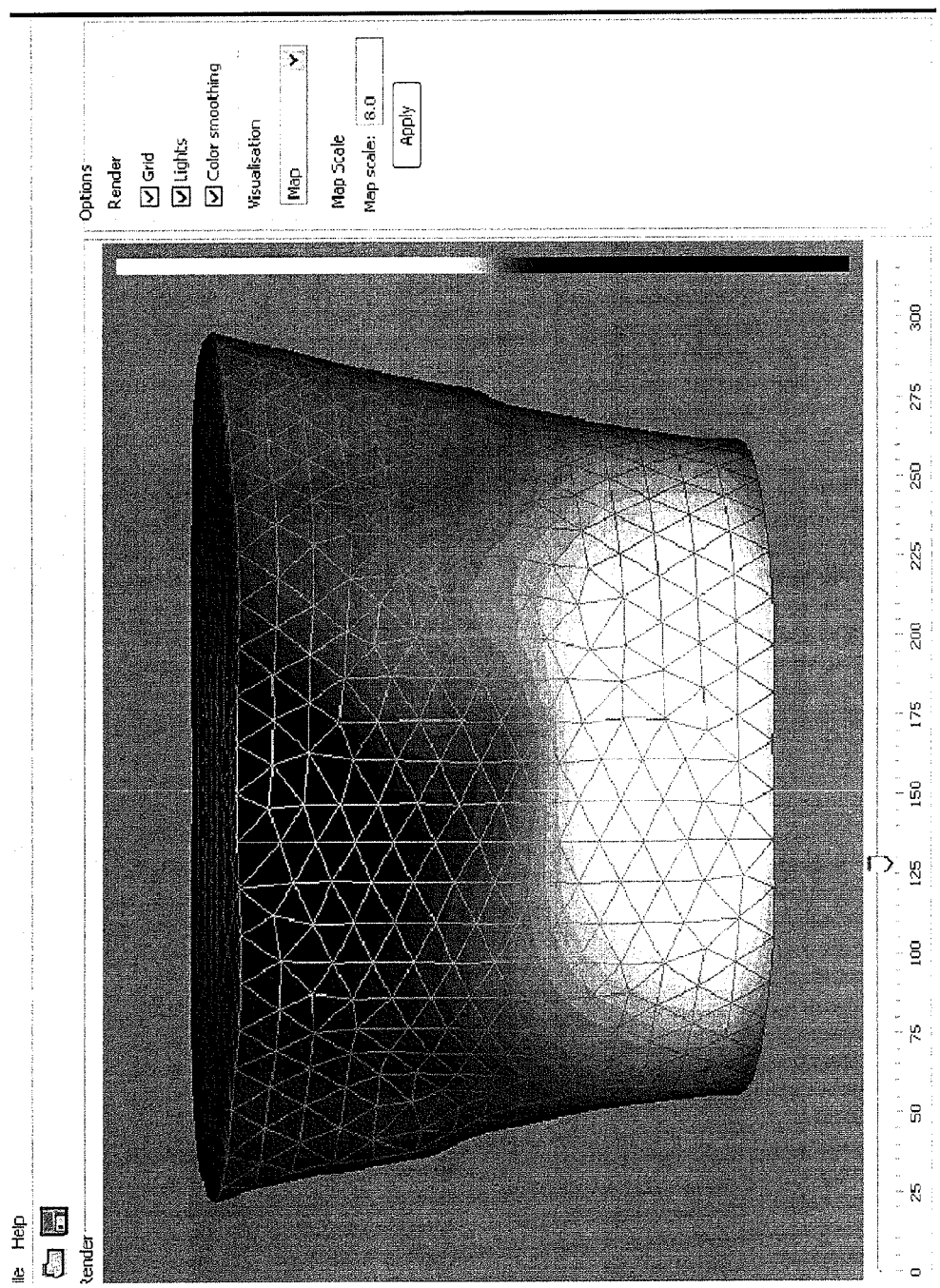
FIG. 10 presents isopotential maps on the torso surface.
Figure 11:
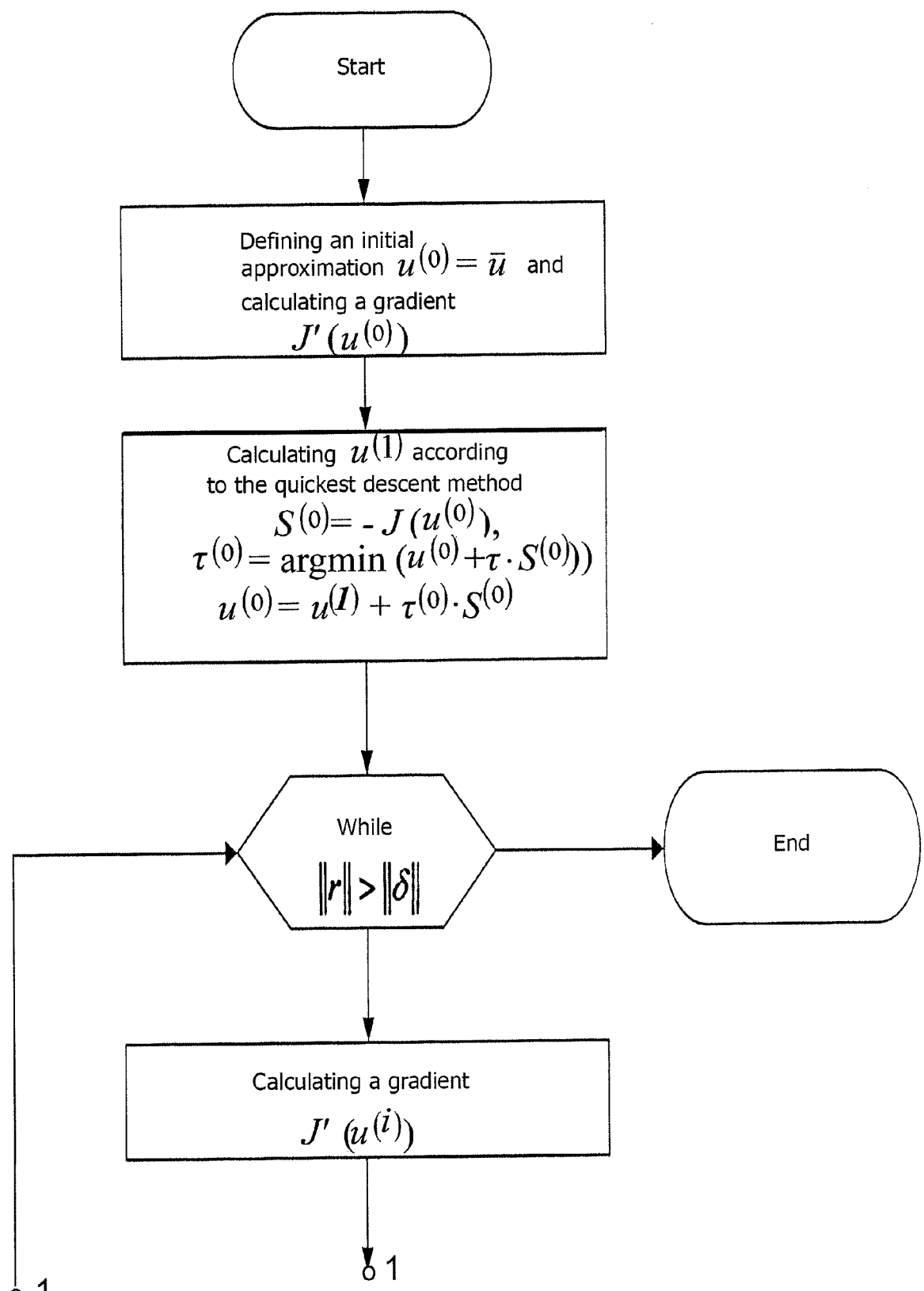
FIG. 11 shows a block-diagram of a computational algorithm of solution of the inverse problem of electrocardiography on the basis of the conjugate gradient method.
Figure 11:
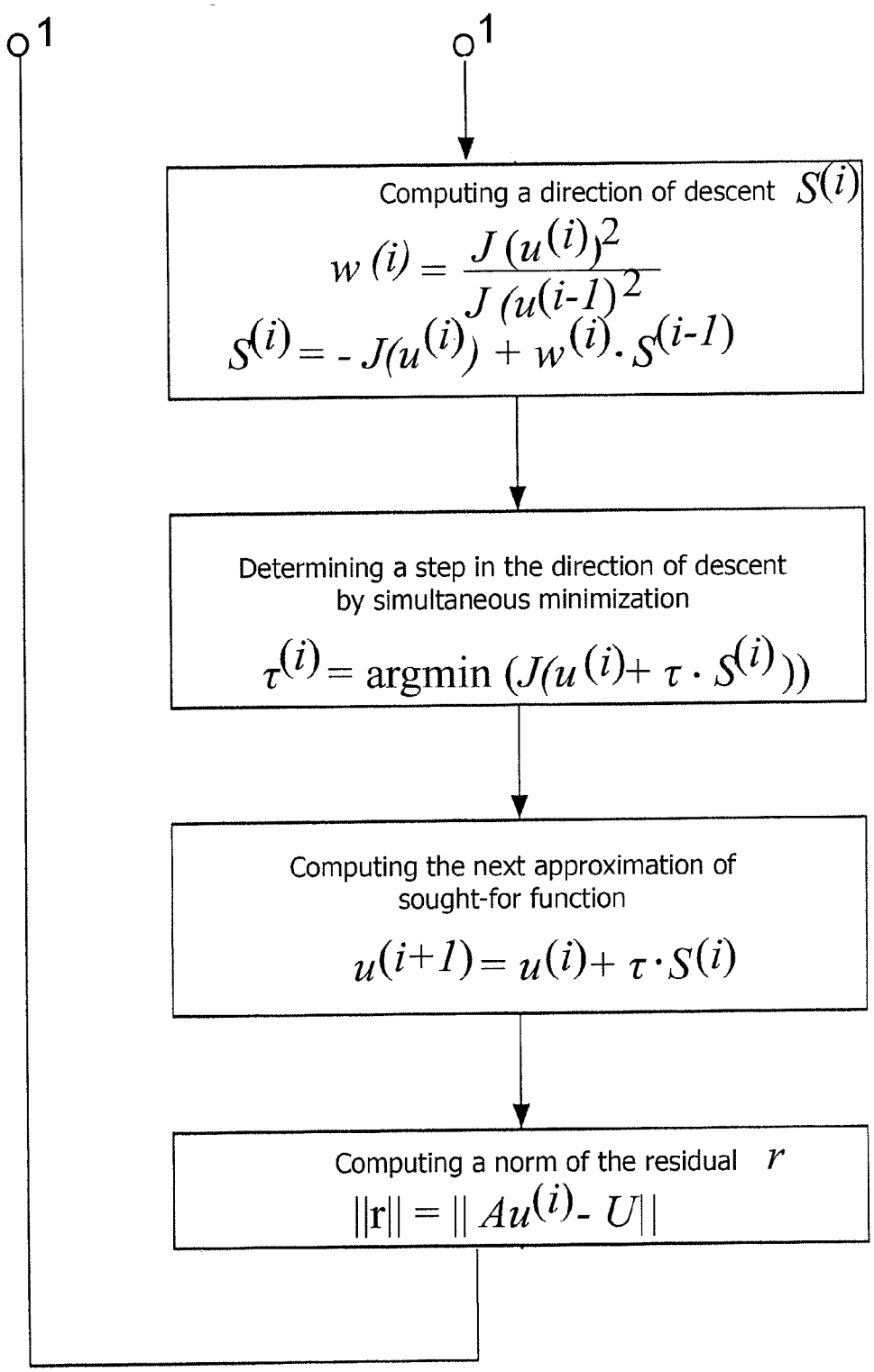
Figure 12:
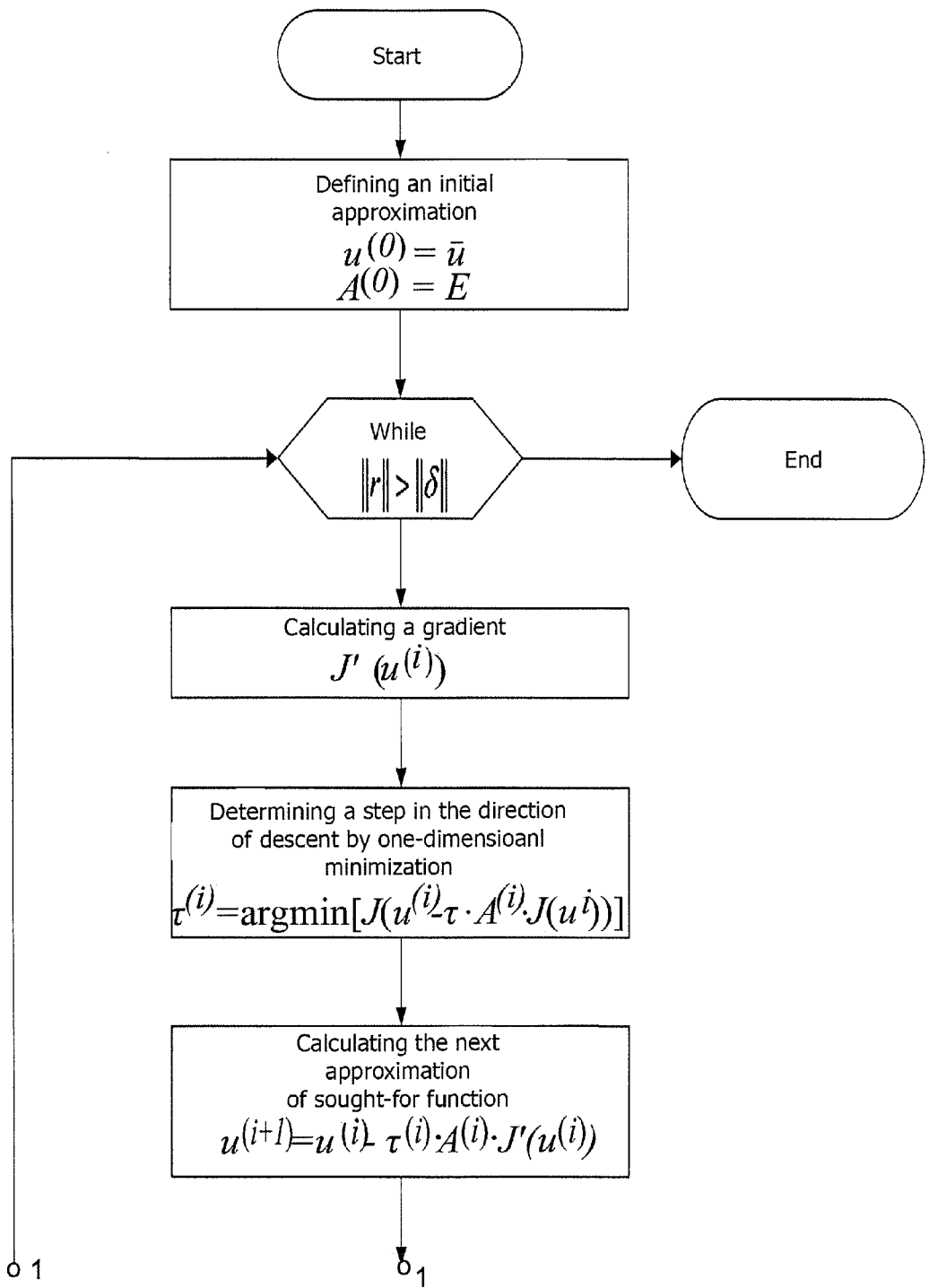
FIG. 12 shows a block-diagram of a computational algorithm of solution of the inverse problem of electrocardiography on the basis of quasi-Newton methods.
Figure 12:
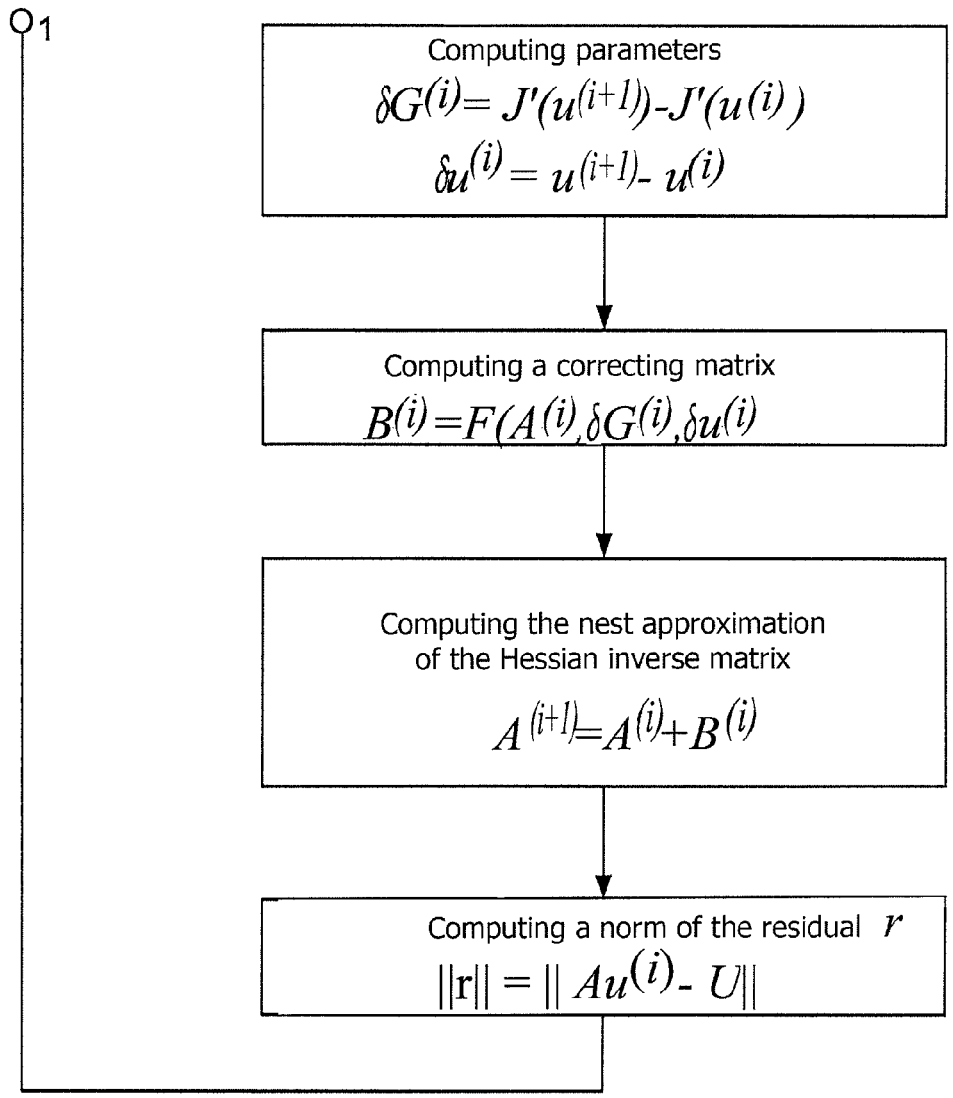
Figure 13:
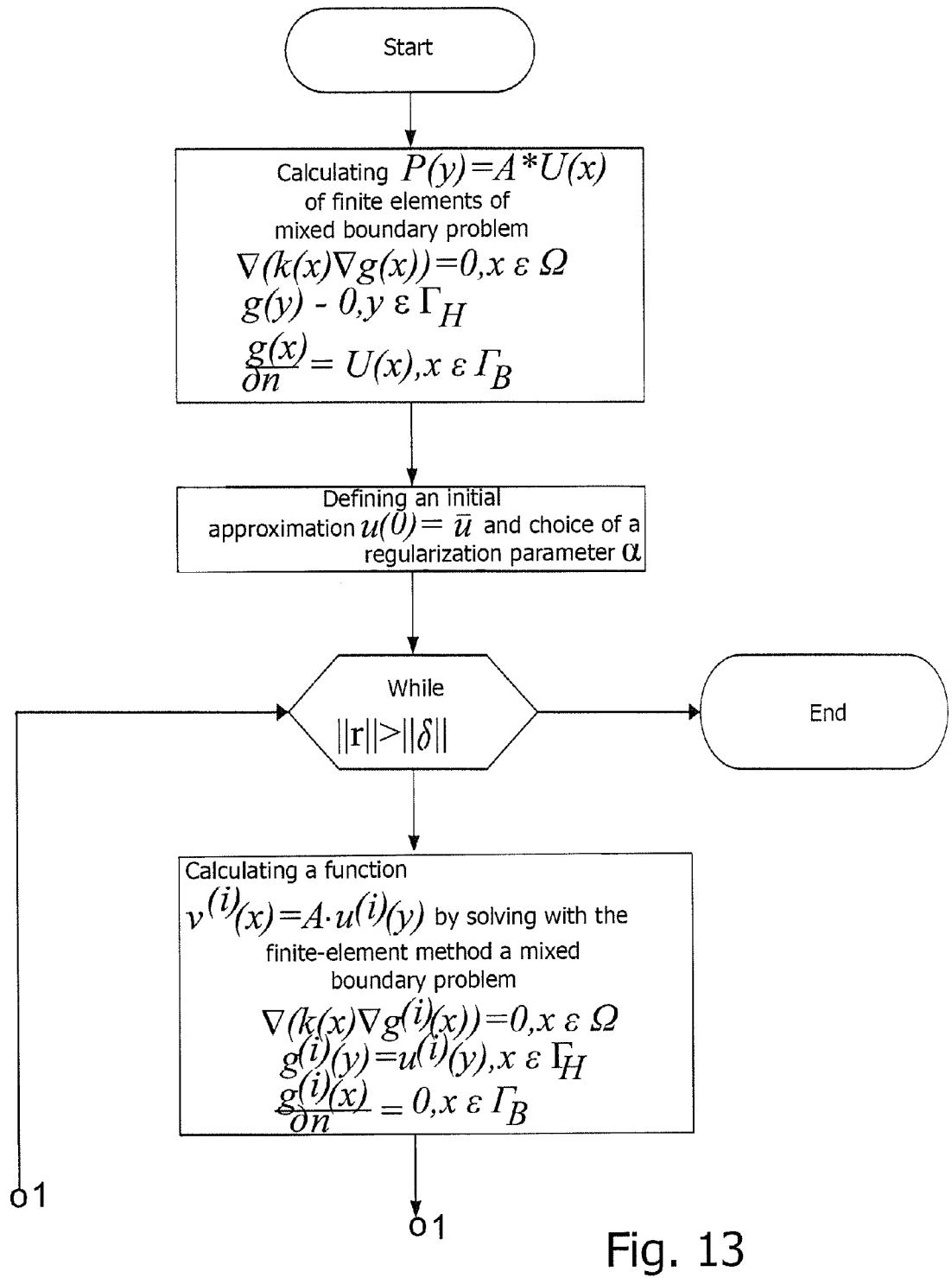
FIG. 13 shows a block-diagram of a computational algorithm of solution of the inverse problem of electrocardiography on the basis of iteration solution of the Euler equation.
Figure 13:
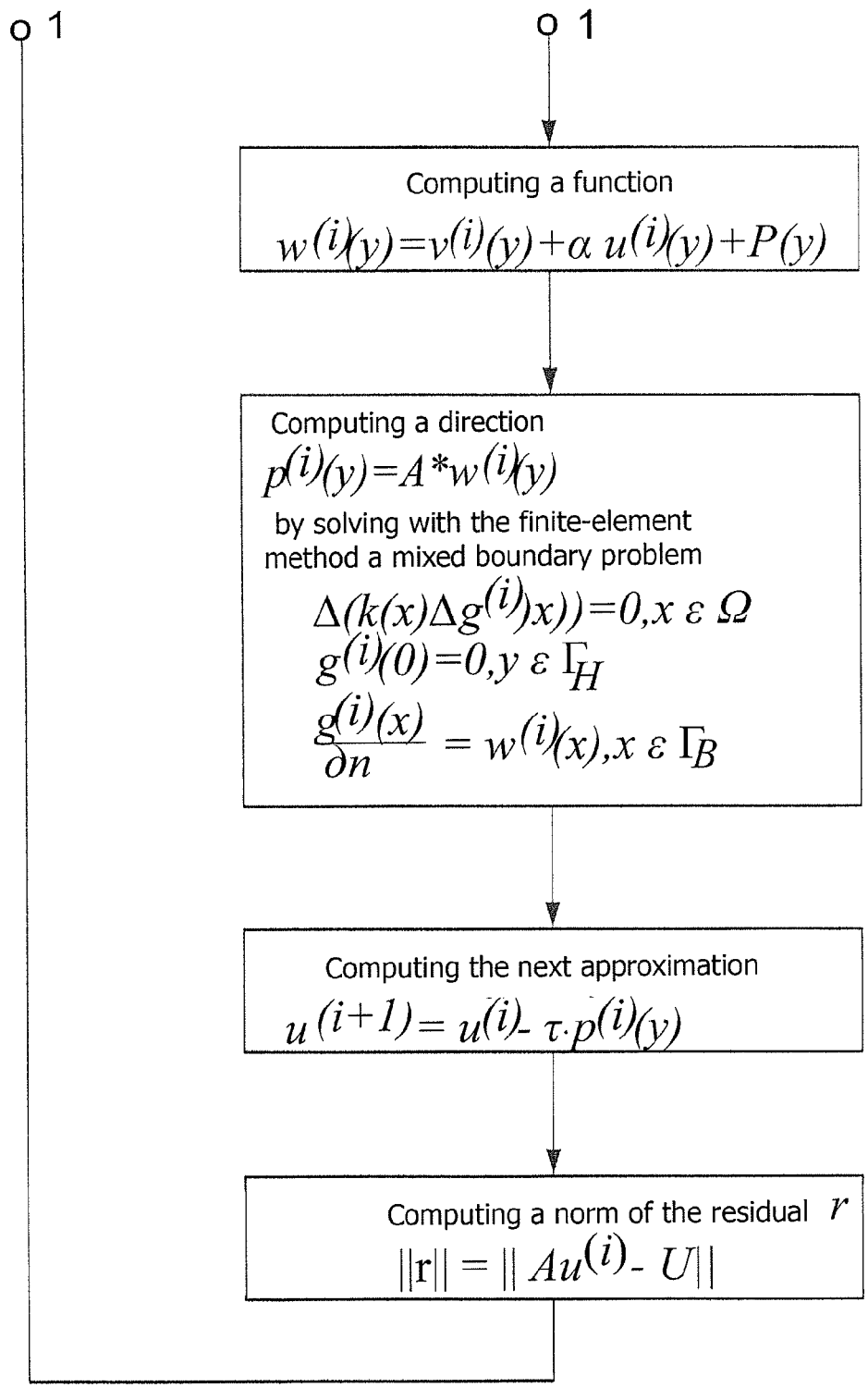

FIG. 10 illustrates constructing isopotential maps on the torso surface.

Constructing isopotential maps is performed by surface interpolation of ECG-signal values at each discrete moment with using radial basis functions.

The electric field potential on the chest surface, S, is represented in the form of a decomposition according to the system of radial basis functions (RBF):

$$U(x) = \Sigma a_j f_j(x), x \in S,$$

where $U(x)$ is the electric field potential, $f_j(x)$ are radial basis functions, $a_j$ are indefinite coefficients.

As RBF, functions of the following kind given at ECG-registration points are used $$f_j(x) = \exp\left(-\frac{\|x - x_j\|}{c^2}\right),$$

where x is a random point on the body surface, $x_j$ are ECG-registration points, $\|x-x_j\|$ is the minimal length of a line belonging to the surface S and connecting points x and $x_j$, c is an experimentally chosen coefficient that determines approximation properties of a function.

Coefficients $a_j$ are found from the condition for the minimum of functional J:

$$J = \frac{1}{2} \sum_{i=1}^{N} \left[\left(\sum_{j=1}^{N} a_j f_j(x_i) + a_0\right) - U(x_i)\right]^2$$

provided that $$\sum_{j=0}^{N} a_j = 0,$$

where $U(x_i)$ are values of the electric field potential at $x_i$ points of ECG-registration on the chest surface, N is a number of ECG-registration points.

For finding coefficients $a_j$, the corresponding system of linear algebraic equations with a matrix of N×N size is solved.

The potential $U(x_t)$ is calculated in nodes of the torso triangulation surface $x_t$ according to the formula $$U(x_i) = \sum_{j=1}^{N} a_j f_j(x_i) + a_0.$$

To calculate the potential at each point of the torso surface, a bilinear interpolation on values in vertices of a grid triangle, which this point belongs to, is applied.

The claimed method includes a method for noninvasive reconstructing the heart electric field potential at internal points of the chest on measured values of the electric field potential on the chest surface by a numerical solution of the inverse problem of electrocardiography for a model of the chest with a variable electroconductivity coefficient with using the finite element method based on iteration algorithms.

For realizing this method, the following model is used. Let $\Omega \epsilon R^3$ be a part of the chest bounded by a sufficiently smooth border $\partial\Omega$, which includes the torso surface being in contact with external medium $\Gamma_B$, cross-sections of the chest at the level of the diaphragm and clavicles $\Gamma_{T1}$ и $\Gamma_{T2}$, as well as the heart epicardial surface $\Gamma_E$. Chest tissues in domain $\Omega$ are assumed to have a variable continuous positive limited specific electroconductivity coefficient $k(x), x \epsilon \Omega \cup \partial\Omega$.

The heart electric field potential in domain $\Omega$ is assumed to satisfy the Laplace equation in an inhomogeneous medium:

$$\nabla(k(X)\nabla u(X))=0, \quad (1)$$

where $X=(x_1, x_2, x_3)^T \epsilon \Omega \subset R^3$ is a point in three-dimensional (3D) space, $$\nabla \equiv \left(\frac{\partial}{\partial x_1}, \frac{\partial}{\partial x_2}, \frac{\partial}{\partial x_3}\right)$$

is the Hamilton operator in $R^3$.

At the part of border $\Gamma_B$ of domain $\Omega$, the Dirichlet condition (electric field potential measured as a result of surface ECG mapping) is assumed to be known $$u(x)=U(x), x \epsilon \Gamma_B, u \epsilon L_2(\Gamma_B) \quad (2)$$

The Dirichlet condition contains a noise component as the result of experimental measurements:

$$U(x)=u_0(x)+\xi(x), x \epsilon \Gamma_B, u_0 \epsilon C^{2,\delta}, \xi \epsilon \Gamma_2(\Gamma_B), \quad (3)$$

where $u_0(x)$ is the exact value of the potential on the chest surface, $\xi(x)$ is an measurement error estimated as $\|\xi(x)\|_{L_2} > \delta$.

At the same border part, the Neumann condition is also known:

$$\frac{\partial u(x)}{\partial n} = P(x) = 0, x \epsilon \Gamma_B, P \epsilon L_2(\Gamma_B), \quad (4)$$

where $$\frac{\partial u(x)}{\partial n}$$

is a potential derivative u(x) along an internal normal to the surface.

Solution of the inverse problem of electrocardiography consists in finding in the class of functions $L_2(\Gamma_H)$ a potential trace u(y) on the surface $\Gamma_H$ that satisfies the Laplace equation in domain $\Omega$ (4) and the boundary conditions (5)-(7) at borders of regions.

Let us raise the following auxiliary problems.
1. It is required to find a potential u(X) such as that:

$$\nabla(k(X)\nabla u(X)) = 0, X \in \Omega, \quad (5)$$

$$u(y) = v(y), y \in \Gamma_H \quad (6)$$

$$\frac{\partial u}{\partial n}(x) = g(x) = 0, x \in \Gamma_B. \quad (7)$$

$$v \in L_2(\Gamma_H), g \in L_2(\Gamma_B)$$

Let us name this problem as a direct one in respect of the inverse boundary problem under study.
2. It is required to find a potential u(X) such as that:

$$\nabla(k(X)\nabla u(X)) = 0, X \in \Omega \quad (8)$$

$$u(y) = v(y), y \in \Gamma_H \quad (9)$$

$$\frac{\partial u}{\partial n}(x) = g(x), x \in \Gamma_B \quad (10)$$

$$v \in L_2(\Gamma_H), g \in L_2(\Gamma_B)$$

Let us name this problem as a conjugate problem in respect of the direct problem.

Let u(y) be a trace of solution of the direct problem (5)-(7) on the surface $\Gamma_B$. Let us introduce an operator of the direct problem A that reflects the given on the surface $\Gamma_H$ Dirichlet condition v(y) into the trace of solution of the direct problem u(x) on the surface $\Gamma_B$, multiplied by an electroconductivity coefficient k(x), $x \epsilon \Gamma_B$ at fixed and equal-to-zero Neumann condition on $\Gamma_B$:

$$A \cdot v(y)=k(x) \cdot u(x),$$

$$v \epsilon L_2(\Gamma_H), k \epsilon L_2(\Gamma_B), u \epsilon L_2(\Gamma_B) \quad (11)$$

Then, solution of the inverse problem is reduced to solution of an operator equation regarding an unknown function v(y):

$$A \cdot v(y)=k(x) \cdot U(x) \quad (12)$$

Let us introduce a quadratic functional:

$$J(v) \equiv \frac{1}{2}\|A \cdot v - k \cdot U\|^2_{L_2(\Gamma_B)} \equiv \frac{1}{2}\int_{\Gamma_B} (A \cdot v(x) - k(x) \cdot U(x))^2 ds \quad (13)$$

This functional is positive and strongly convex, and its exact lower border equals to zero. Therefore, a problem of solving the equation (12) and a variation problem of finding the function v, on which the present functional reaches its minimum, are equivalents:

v=arg min J(v).

The claimed method includes algorithms of solution of the inverse problem of electrocardiography by numerical minimization of functional (13) based on methods of gradient optimization or iteration solution of the Euler equation that is a necessary condition for the minimum of functional. Algorithms indicated are iteration ones, at each iteration a solution of direct and conjugate problems by the boundary element method being performed.

According to Hadamard, the problem of minimization of functional (13) is ill-posed because of an incorrect statement of the inverse problem of electrocardiography.

The claimed method involves algorithms of solution of the inverse problem of electrocardiography by numerical minimization of functional (13) with using regularization methods based on restricting a number of iterations and on the Tikhonov method.

A computational algorithm includes the following steps.

1. Finite-element discretization of computational domain is carried out: domain Ω is split into tetrahedral elements and its borders $\Gamma_H$ and $\Gamma_{H'}$—into triangle elements, functions u(x), $x \in \Gamma_{H'}$ $$p(x) \equiv \frac{\partial u(x)}{\partial n},$$

$x \in \Gamma_H$, U(x), $x \in \Gamma_{H'}$, U(x), $x \in \Gamma_B$, $$u(x) = \sum_{i=1}^{N} u_i \cdot \varphi_i(x), x \in \Gamma_H, p(x) = \sum_{i=1}^{N} p_i \cdot \varphi_i(x), x \in \Gamma_H$$

$$U(x) = \sum_{i=1}^{M} U_i \cdot \varphi_i(x), x \in \Gamma_H, P(x) = \sum_{i=1}^{M} P_i \cdot \varphi_i(x), x \in \Gamma_H,$$

$x \in \Gamma_B$ being represented in the form of:

$$P(x) \equiv \frac{\partial u(x)}{\partial n},$$

where $u_i$, $p_i$, $P_i$, $U_i$ are values of functions u(x), p(x), U(x), P(x) in surface nodes of a finite-element grid, $\phi_i(x)$ are linearly independent finite basis functions given in nodes of a finite-element grid.

2. Vector $u = \{u_1, u_2, \ldots, u_n\}$ is computed based on an iteration procedure of numerical minimization of functional (21).

3. Function u(x), $x \in \Gamma_H$, which is a final solution of the problem, is found according to the formula:

$$u(x) = \sum_{i=1}^{N} u_i \cdot \varphi_i(x).$$

The method includes the following iteration methods for finding a vector $u = \{u_1, u_2, \ldots, u_n\}$. See: (Gill F., Murray Y, Wright M Practical optimization [Russian translation]. Moscow: Mir, 1985).

1. The conjugate gradient method (the Fletcher-Reeves method)

$$u^{(0)} = \overline{u},$$

$$S^{(0)} = -J'(u^{(i)}),$$

$$w^{(i)} = \frac{J(u^{(i)})^2}{J(u^{(i-1)})^2}$$

$$S^{(i)} = -J'(u^{(i)}) + \omega^{(i)} \cdot S^{(i-1)},$$

$$\tau^{(i)} = \operatorname{argmin}(J(u^{(i)} + \tau \cdot S^{(i)})),$$

$$u^{(i+1)} = u^{(i)} + \tau \cdot S^{(i)},$$

where i=1, 2 . . . , N is the iteration number, $u^{(0)} = \{u_i^0, u_2^0, \ldots, u_n^0\}$ is an initial approximation of vector u, $u^{(i)} = \{u_1^i, u_2^i, \ldots u_n^i\}$ is the next approximation of vector u.

Exit from an iteration procedure is performed according to the principle of the residual (the Morozov principle): an iteration process is stopped as soon as the following condition is reached:

$$2\sqrt{J(u^{(i)})} \leq \delta.$$

When reaching the iteration number, divisible by m, it is assumed that:

$S^{(im)} = S^{(0)}$ where m is an integer parameter being chosen by an experimental way.

2. Quasi-Newton methods, which involve a gradient descent method (the Cauchy method) and the Newton method but use iterative ways for computing the Hessian inverse matrix $$u^{(0)} = \overline{u},$$

$$A^{(0)} = E$$

$$\tau = \arg \min[J(u^{(i)} - \tau^{(i)} \cdot A^{(i)} \cdot J'(u^i))],$$

$$u^{(i+1)} = u^{(i)} - \tau^{(i)} \cdot A^{(i)} \cdot J(u^{(i)}),$$

$$\delta G^{(i)} = J'(u^{(i+1)}) - J'(u^{(i)}),$$

$$\delta u^{(i)} = u^{(i+1)} - u^{(i)},$$

$$A^{(i+1)} = A^{(i)} + B^{(i)},$$

where $A^{(i)}$ is the next approximation of the Hessian inverse matrix of functional J(u), E is a unit matrix, $B^{(i)}$ is a correcting matrix being computed by different techniques described lower.

2.1. The Davidon-Fletcher-Powell method $$B^{(i)} = \frac{\delta u^{(i)} \cdot \delta u^{(i)T}}{\delta u^{(i)T} \cdot \delta G^{(i)}} - \frac{A^{(i)} \cdot \delta G^{(i)} \cdot \delta G^{(i)T} \cdot A^{(i)}}{\delta G^{(i)T} \cdot A^{(i)} \cdot \delta G^{(k)}}.$$

2.2. The Broyden-Fletcher-Shanno method $$B^{(i)} = \left[E - \frac{\delta u^{(i)} \cdot \delta G^{(i)T}}{u^{(i)T} \cdot \delta G^{(i)}}\right] \cdot A^{(i)} \cdot \left[E - \frac{\delta u^{(i)} \cdot \delta G^{(i)T}}{u^{(i)T} \cdot \delta G^{(i)}}\right] + \frac{\delta u^{(i)} \cdot \delta u^{(i)T}}{\delta u^{(i)T} \cdot \delta G^{(i)}}.$$

2.3. Pierson's methods $$B^{(i)} = \frac{(\delta u^{(i)} - A^{(i)} \cdot \delta G^{(i)}) \cdot \delta u^{(i)T}}{\delta u^{(i)T} \cdot \delta G^{(i)}}.$$

$$B^{(i)} = [\delta u^{(i)} - A^{(i)} \cdot \delta G^{(i)}] \cdot \frac{[A^{(i)} \cdot \delta G^{(i)}]^T}{\delta G^{(i)T} \cdot A^{(i)} \cdot \delta G^{(i)}}.$$

Exit from an iterative procedure is performed according to the principal of the residual (the Morozov principle): an iteration process is stopped as soon as the following condition is reached:

$$2\sqrt{J(u^{(i)})} \leq \delta.$$

When reaching the iteration number, divisible by m, it is assumed that:

$A^{(im)} = A^{(0)}$ where m is an integer parameter being chosen by an experimental way.

In iterative procedures described, it is necessary to compute a functional $J(u^i)$ and its gradient $J'(u^{(i)})$.

The method includes calculations of the indicated objects by the following methods.

1. Calculation of $J(u^i)$.

1.1. The function $v^{(i)}(x)$, $x\in\Omega$ is found by solving the following mixed boundary problem for the Laplace equation in an inhomogeneous medium with using the boundary element method (the direct problem (5)-(7)):

$$\nabla(k(x)\nabla v^{(i)}(x)) = 0, x \in \Omega,$$

$$v^{(i)}(x) = u^{(i)}(x), x \in \Gamma_H.$$

$$\frac{v^{(i)}(x)}{\partial n} = 0, x \in \Gamma_B.$$

A solution trace $v^{(i)}(x)$ at the border $\Gamma_B$ is found.

$J(u^{(i)})$ is calculated by numerical integration according to the formula:

$$J(u^{(i)}) = \frac{1}{2}\|k(x)\cdot(v^{(i)}(x) - U(x))\|^2_{L_2(\Gamma_B)} \equiv \frac{1}{2}\int_{\Gamma_B} k(x)\cdot(v^{(i)}(x) - U(x))^2 ds,$$

$$x \in \Gamma_B.$$

2. Calculation of $J'(u^{(i)})$.

2.1. The function $g^{(i)}(x)$, $x\in\Omega$ is found by solving the following mixed boundary problem for the Laplace equation in an inhomogeneous medium with using the boundary element method (the conjugate problem (8)-(10)):

$$\nabla(k(X)\nabla g^{(i)}(X)) = 0, X \in \Omega,$$

$$g^{(i)}(y) = 0, x \in \Gamma_H,$$

$$\frac{g^{(i)}(x)}{\partial n} = k(x)\cdot(u^{(i)}(x) - U(x)), x \in \Gamma_B.$$

2.2. A normal derivative of solution at the border $\Gamma_H$:

$$\frac{\partial g^{(i)}(H)}{\partial n},$$

$x\in\Gamma_H$ is calculated by numerical differentiation of the found solution $g^{(i)}(x)$.

2.3. The obtained normal derivative is multiplied by a coefficient of electroconductivity $k(y)$ with inverse sign on the surface $\Gamma_H$:

$$p^{(i)}(y) = -k(y)\cdot\frac{\partial g^{(i)}(y)}{\partial n}, x \in \Gamma_H.$$

3.3. Values of the obtained function $p^{(i)}(x)$, $x\in\Gamma_H$ in surface nodes of a boundary-element grid are assumed to be values of vector $J'(u^{(i)})$:

$$J'(u^{(i)})=\{p_1^{(i)}, p_2^{(i)}, \ldots, p_n^{(i)}\}.$$

The method involves a minimization of functional (13) based on numerical solution of the Euler equation that is the necessary condition for the minimum of functional (13):

$$A^*A\cdot u = A^*U, \quad (14)$$

where $A^*$ is an operator conjugate to the operator $A$.

Solving the equation (11) is performed on the basis of the following iteration algorithm:

$$u^{(0)} = \bar{u},$$

$$u^{i+1} = u^{(i)} - \tau\cdot(A^*\cdot A\cdot u^{(i)} - A^*\cdot U),$$

where $\bar{u}$ is a random initial approximation, $i=1, 2, \ldots, n$ is the iteration number, $\tau$ is a parameter of an iterative method.

Exit from an iterative procedure is implemented according to the principle of the residual:

The iterative process is stopped when the following condition is reached:

$$\|A\sim u^{(i)} - U\| \leq \delta.$$

An algorithm can be written in a more detailed form:

$$P(y) = A^*U(x),$$

$$u^{(0)}(y) = \bar{u}(y),$$

$$v^{(i)}(x) = A\cdot u^{(i)}(y),$$

$$p^{(i)}(y) = A^*\cdot v^{(i)}(x)$$

$$u^{i+1}(y) = u^{(i)}(y) - \Gamma\cdot(p^{(i)}(y) - P(y)),$$

$x\in\Gamma_B, y\in\Gamma_H.$

Calculations of the function $P(y)=A^*U(x)$ are carried out by the following way. 1. With using the finite element method, the following mixed boundary problem for the Laplace equation in an inhomogeneous medium is solved (the conjugate problem (8)-(10)):

$$\nabla(k(X)\nabla g(X)) = 0, X \in \Omega,$$

$$g(y) = 0, y \in \Gamma_H,$$

$$\frac{g(x)}{\partial n} = U(x), x \in \Gamma_B,$$

2. By numerical differentiation of the found solution $g(y)$, a normal derivative of solution at the border $\Gamma_H$:

$$\Gamma_H : \frac{\partial g(y)}{\partial n},$$

$y\in\Gamma_H$ is calculated.

3. The obtained normal derivative is multiplied by a coefficient of electroconductivity $k(y)$ with inverse sign at the border $\Gamma_H$:

$$P(y) = -k(y)\cdot\frac{\partial g(y)}{\partial n}, y \in \Gamma_H$$

Calculation of functions $p(y)=A^*v^{(i)}(x)$ is carried out by the same way.

1. With using the finite element method, the following mixed boundary problem for the Laplace equation in an inhomogeneous medium is solved at each iteration (the conjugate problem (8)-(10)):

$$\nabla(k(X)\nabla g^{(i)}(X)) = 0, X \in \Omega,$$

-continued $$g^{(i)}(0) = 0, y \in \Gamma_H,$$

$$\frac{g^{(i)}(x)}{\partial n} = v^{(i)}(x), x \in \Gamma_B.$$

2. By numerical differentiation of the obtained solution g(y), a normal derivative of solution is calculated at the border $\Gamma_H$:

$$\Gamma_H : \frac{\partial g^{(i)}(y)}{\partial n},$$

y∈$\Gamma_H$

3. The obtained normal derivative is multiplied by a coefficient of electroconductivity k(y) with inverse sign at the border $\Gamma_H$:

$$\Gamma_H : p^{(i)}(y) = -k(y) \cdot \frac{\partial g^{(i)}(y)}{\partial n},$$

y∈$\Gamma_H$.

Calculation of the function $v^{(i)}(x)=A \cdot u^{(i)}(y)$ is performed by the following way.

1. The function $v^{(i)}(x)$, x∈Ω is found by solving the following mixed boundary problem for the Laplace equation in an inhomogeneous medium with using the boundary element method (the direct problem (5)-(7)):

$$\nabla(k(X)\nabla v^{(i)}(X)) = 0, X \in \Omega,$$

$$v^{(i)}(y) = u^{(i)}(y), x \in \Gamma_H.$$

$$\frac{v^{(i)}(x)}{\partial n} = 0, x \in \Gamma_B,$$

2. A trace of the obtained solution at the border is multiplied by a coefficient of electroconductivity k(x) at the border $\Gamma_B$:

$$v^{(i)}(x)=k(x) \cdot u(x), x \in \Gamma_B.$$

The method involves a minimization of functional (13) with using the Tikhonov regularization on the basis of solving the corresponding Euler equation:

$$A^*(A+\alpha \cdot I) \cdot u = A^* U, \alpha > 0, \quad (15)$$

where α is a regularization parameter, I is an unit operator.

Solving the equation (15) is implemented based on an iterative procedure:

$$u^{(0)} = \overline{u},$$

$$u^{(i+1)} = u^{(i)} - \tau \cdot (A^* \cdot (A \cdot u^{(i)} + \alpha \cdot u^{(i)} - A^* \cdot U).$$

Exit from an iterative procedure is performed when the following condition is reached:

$|u_{i+1} - u_i| < \epsilon$ where $\epsilon$ is a small positive parameter depending on the machine accuracy.

The choice of a regularization parameter α is carried out according to the principle of the residual: such α is chosen at which the following equality is fulfilled the most exactly:

$$\|A \cdot u(\alpha) - U\| = \delta,$$

where u(α) is a parameter α-depending solution obtained as a result of implementing the iterative procedure.

Block-diagrams of algorithms are shown in FIG. 1, 12, 13.

Figure 14A:
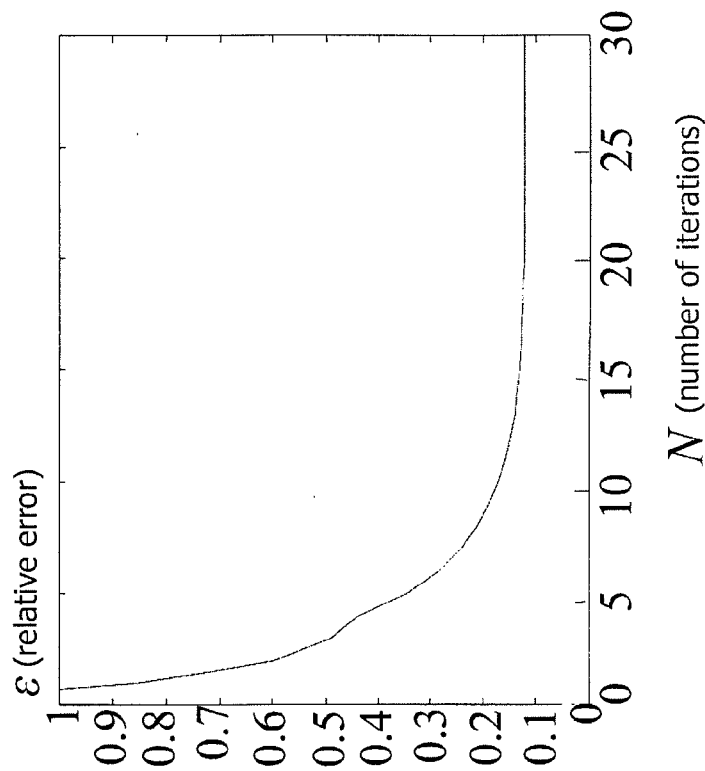
FIG. 14 depicts a convergence diagram of an iterative procedure for the Davidon-Fletcher-Powell method (A) and for an iteration method of solution of the Euler equation (B).
Figure 14B:
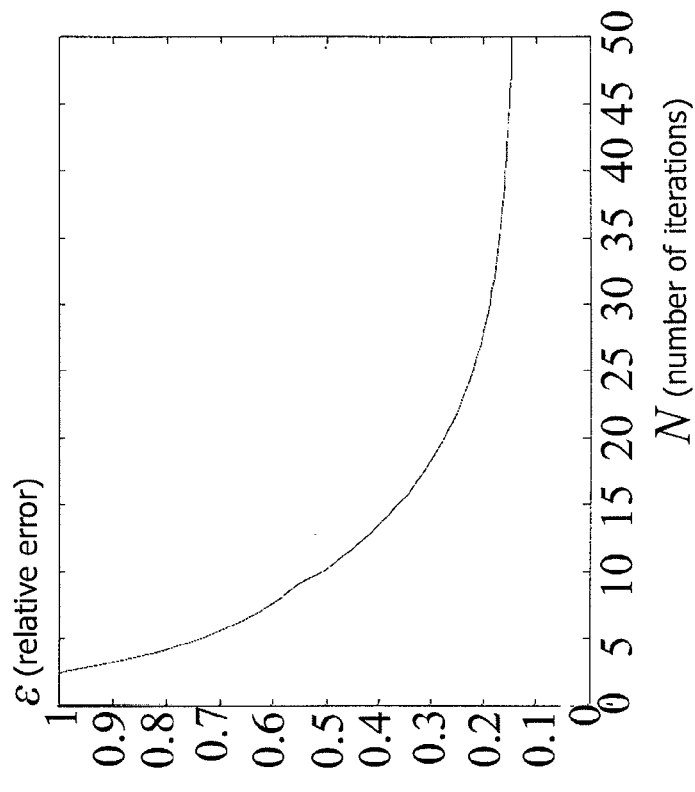

FIG. 14 gives convergence diagrams of a quasi-Newton iterative procedure of Davidon-Fletcher-Powell (14A) and of iteration solution of the Euler equation (14B).

In calculations, a model of the torso and heart of a real patient was used. For modeling the standard electric field of the heart, a quadruple source to be placed in the geometric center of the heart was used.

Figure 15A:
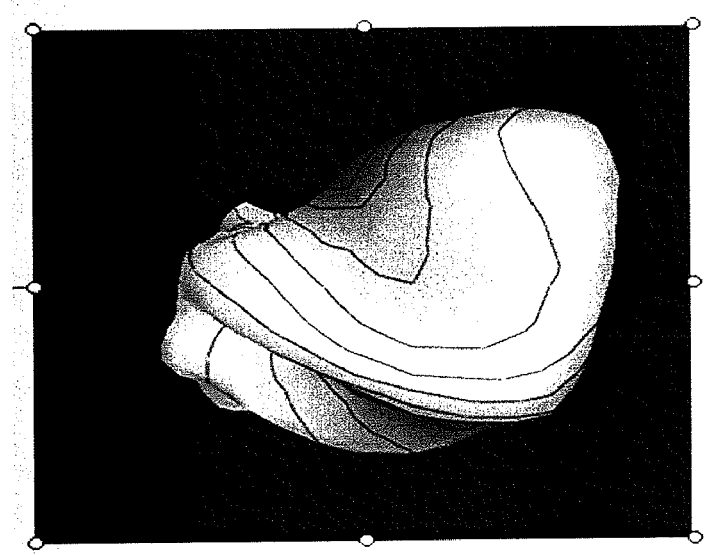
FIG. 15 shows results of electric field reconstructing on the heart surface for an inhomogeneous model (B) and for a homogeneous model (C). Standard reconstructing is shown in FIG. 15A.
Figure 15B:
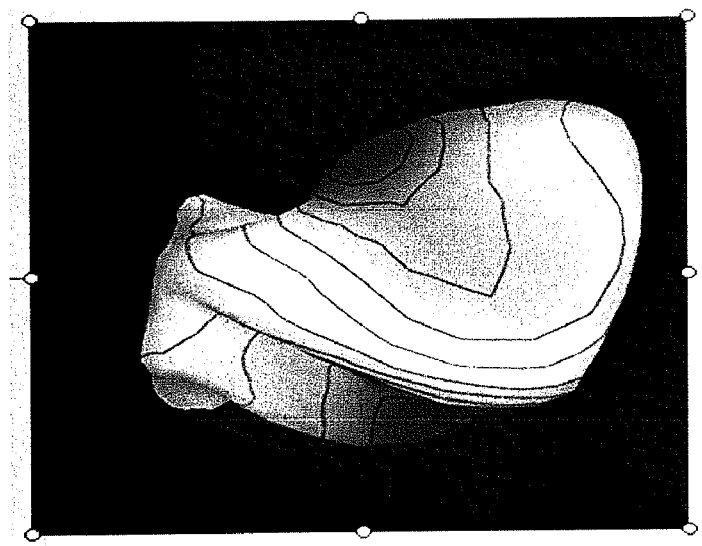
Figure 15C:
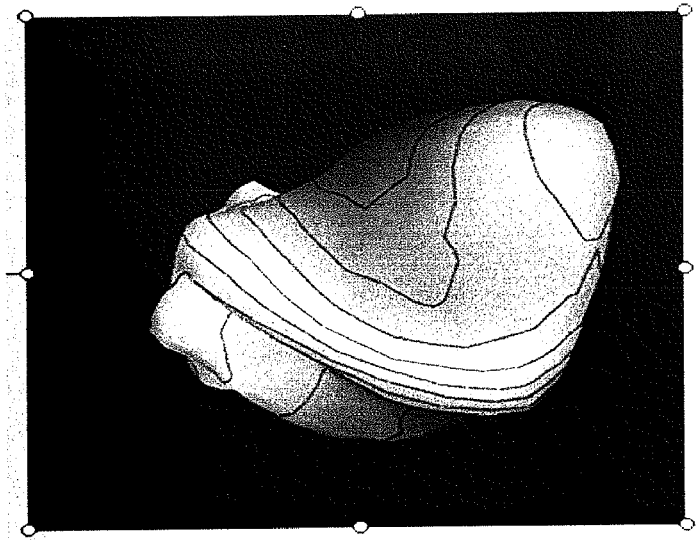

FIG. 15 gives imposed on realistic models of the heart isopotential maps of the exact electric potential (14A) calculated by the disclosed in the present invention algorithm with taking into account an electrical inhomogeneity of the chest (14B) and by an algorithm based on a homogeneous model of the chest and disclosed in the patent-prototype of the present invention (14C).

FIG. 16 shows examples of visualizing results of noninvasive electrophysiological study of the heart.

Figure 16D:
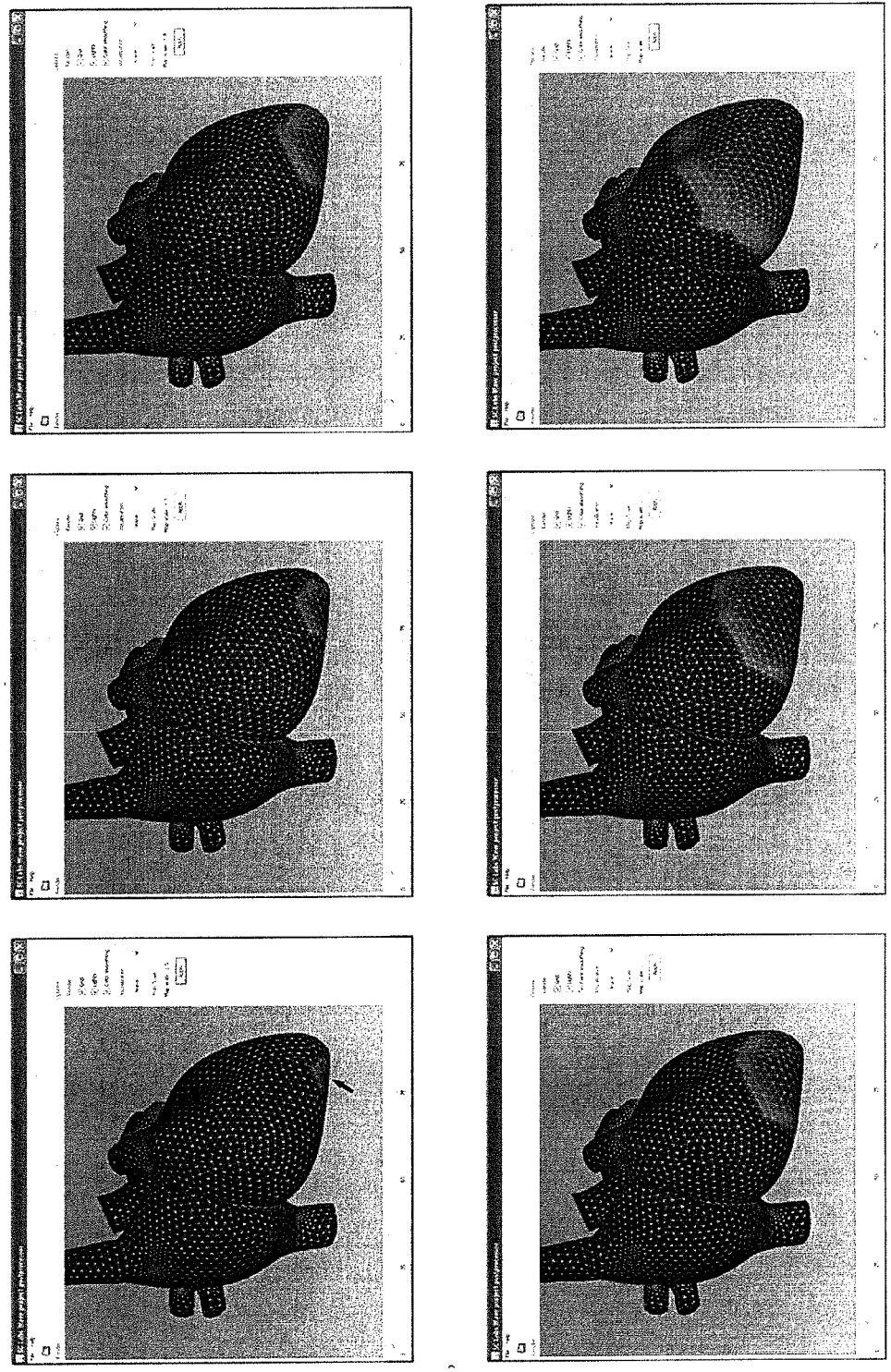
FIG. 16 shows examples of visualizing results of noninvasive electrophysiological study of the heart.

The following kinds of visual representation are used:
1. Constructing electrograms at interactively chosen points of the heart epicardial surface, endocardial surfaces of interventricular and interatrial septa, as well as at internal points of the chest on tomography cross-sections (FIG. 16A).
2. Constructing isopotential maps on tomography cross-sections of the chest (FIG. 16B).
3. Constructing isopotential and isochronous maps on the heart epicardial surface, endocardial surfaces of interventricular and interatrial septa (FIG. 16C).
4. Visualizing the dynamics of the myocardium excitation on the heart epicardial surface, endocardial surfaces of interventricular and interatrial septa in animation mode (propagation maps) (FIG. 16D).

Unipolar electrograms are constructed by interpolation of computed values of the heart electric field potential for all the moments of the cardiocycle at a given point. Bipolar electrograms are constructed as the difference of electrograms in chosen node and at the point located in the vicinity to this node at a distance Δl in the direction to I. Parameters Δl and l are interactively given.

Isopotential maps are constructed on the basis of bilinear interpolation of computed values of the heart electric field potential in nodes of a grid at given moment of the cardiocycle by a gradient painting method or constructing isopotential lines.

For constructing isochronous maps two modes—manual and automatic—are provided. In manual mode at interactively chosen node of a grid an unipolar electrogram U(t), bipolar electrogram $U_b=U_1(t)-U_2(tt)$, as well as a differential electrogram $$U^I(t) = \frac{dU(t)}{dt},$$

i.e., a diagram of first derivative of an unipolar electrogram over time, are reconstructed. An operator in interactive mode marks in indicated diagrams a time-point τ corresponding to the start of the myocardium activation at a given point. The choice of corresponding mark of a time-point τ in automatic mode proceeds without operator's interference. The time-point τ is determined as a maximum of a negative differential unipolar electrogram:

$$\tau = \max\left(-\frac{dU(t)}{dt}\right).$$

Isochronous maps are visualized on the basis of bilinear interpolation of τ values in grid nodes by the gradient painting method or constructing isochronous lines. The same data are represented in animation mode in the form of so-called excitation propagation maps.

Figure 17:
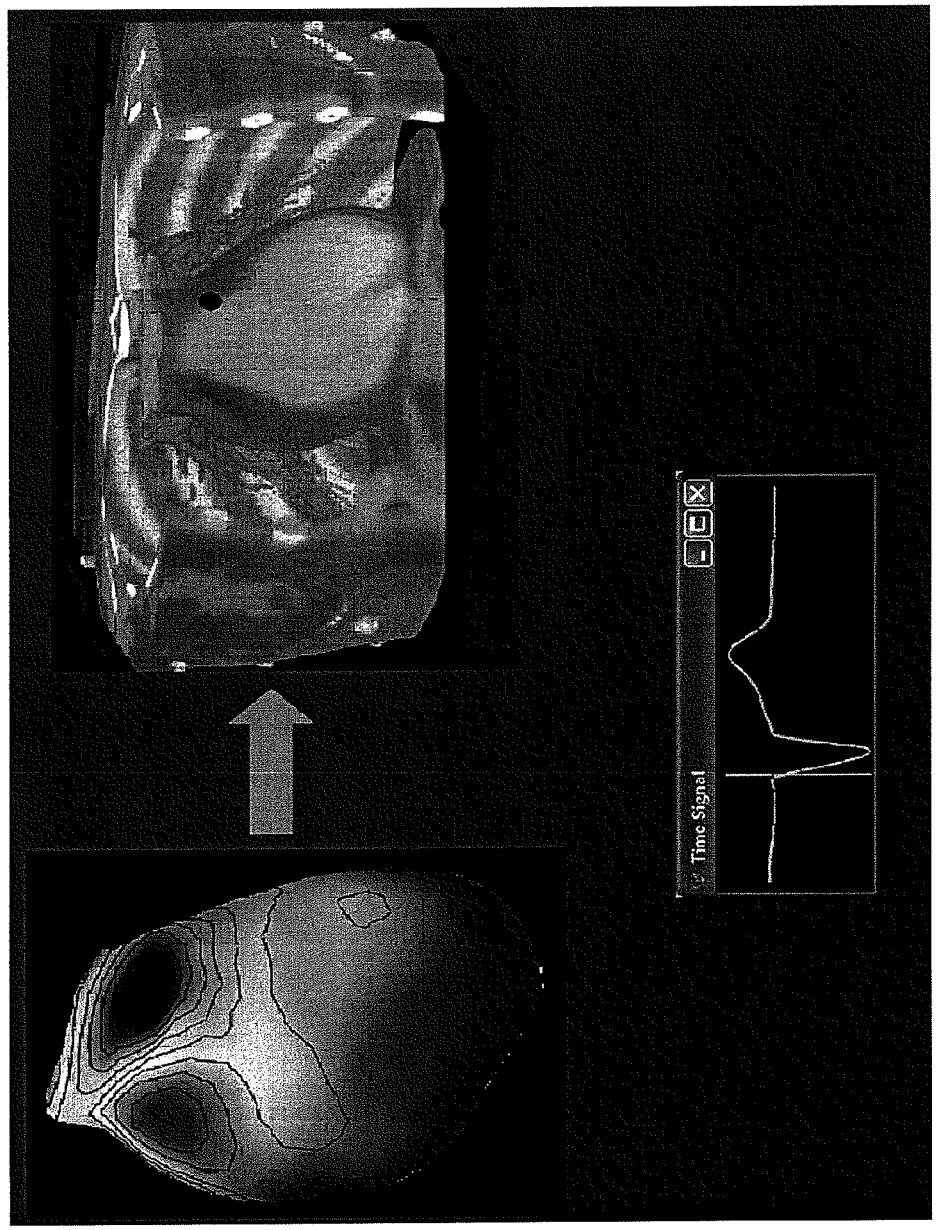
FIG. 17 shows an example of topical diagnosis of an arrhythmogenic source.

FIG. 17 presents reconstructed by the described method epicardial isochronous maps of the extrasystole caused by an ectopic source in the region of excretory tract of the right ventricle. The mini-circle indicates a localization of the ablation electrode with the help of which a successful radio-frequency ablation of this ectopic source was implemented.

What is claimed is:

1. A method for a noninvasive electrophysiological study of the heart, comprising the following steps:
attaching one-off registration electrodes and an ECG-recorder with multiple unipolar leads to a patient's chest and using said electrodes and said recorder for:
processing of ECG-signals in real-time mode,
retrospective processing of the ECG-signals, and
generating a computed tomography (CT) or a magneto-resonance tomography (MRT) of the chest of the patient with the electrodes attached;
constructing and editing computer voxel models of the chest and heart, based on said computed tomography (CT) or said magneto-resonance tomography (MRT) of the chest of the patient with the electrodes attached,
constructing polygonal models of the chest and heart with the help of a computer program, using said voxel models of the chest and heart,
constructing a finite-element grid containing nodes of a region bounded by the external surface of the chest and the heart epicardial surface based on said polygonal models;
determining a specific electroconductivity coefficient of a biological tissue for each said node of the finite-element grid, by determining a type of a biological tissue based on Hounsfield numbers for the patient in said computer tomograms or determining a type of a biological tissue based on values of an MR-signal in said magneto-resonance tomograms;
determining coordinates of the registration electrodes on the chest surface;
interpolating values of the ECG-signals in nodes of said polygonal models therefore obtaining isopotential maps on a polygonal model of the torso;
reconstructing an electric field potential at given points of the chest and heart epicardial, interventricular, and interatrial septum surfaces; and
visualizing, based on said reconstructing step, the reconstructed heart electric field potential in the form of epicardial electrograms, and isochronous and isopotential maps on said polygonal models of the heart.

2. The method according to claim 1, further comprising the steps of using sticky metal chlorine-silver electrodes for the CT, and using sticky graphite electrodes for the MRT.

3. The method according to claim 1, wherein the one-off electrodes are attached in the form of horizontal 5-8 belts positioned at similar distances between the belts the first belt being positioned at the level of a sterno-clavicular articulation and the last belt being positioned at the level of lower edge of the rib surface, and each belt includes from 16 to 30 electrodes located at similar distances in circumference of the chest.

4. The method according to claim 1, wherein a shear-warp factorization of the viewing transformation algorithm is used for constructing the voxel model.

5. The method according to claim 1, wherein constructing the polygonal models comprises the following steps:
filtrating the voxel models for diminishing casual noises;
constructing a triangulation surface by a "marching cubes" method or an "advancing front method";
rarefying and improving the polygonal grid using a Poisson surface reconstruction method.

6. The method according to claim 1, wherein the construction of the finite-element grid is performed by an "advancing front method".

7. The method according to claim 1, wherein the determination of a coefficient of specific electroconductivity of each point of the chest is carried out on the basis of known conformities between a type of the biological tissue and the Hounsfield number (at CT) or between an intensity of a MR-signal (at MRT), on the one part, and a type of the biological tissue and its specific electroconductivity, on the other part.

8. The method according to claim 1, further comprising determining the coordinates of the registration electrodes in automatic mode on the CT or the MRT of the chest.

9. The method according to claim 1, wherein the interpolation of values of the ECG-signals of the polygonal grid is performed using radial basis functions.

10. The method according to claim 1, wherein a numerical solution of a Cauchy problem for a Laplace equation is used for reconstructing the heart electric field potential, this solution being reduced to a numerical minimization of a quadratic functional by gradient methods using a Tikhonov regularization or an iterative regularization and restricting a number of iterations, values of the functional and gradient of the functional at each step of the iteration procedure computed by using the Laplace equation in an inhomogeneous medium by a finite-element method.

11. The method according to claim 10, wherein the quadratic functional minimization is based on a conjugate gradient method called a Fletcher-Reeves method.

12. The method according to claim 10, wherein the quadratic functional minimization is based on a Davidon-Fletcher-Powell method.

13. The method according to claim 10, wherein the quadratic functional minimization is based on a Broyden-Fletcher-Shanno method.

14. The method according to claim 10, wherein the quadratic functional minimization is based on a Pierson's method.

15. The method according to claim 10, wherein the quadratic functional minimization is based on solving a Euler equation by an iteration procedure, the iteration procedure at each step including solutions for direct and conjugate problems of the Laplace equation in an inhomogeneous medium by the finite-element method.

* * * * *